United States Patent [19]

Vyas et al.

[11] Patent Number: 4,866,180

[45] Date of Patent: * Sep. 12, 1989

[54] AMINO DISULFIDE THIOL EXCHANGE PRODUCTS

[75] Inventors: Dolatrai M. Vyas, Fayetteville, N.Y.; Yulin Chiang, Convent Station, N.J.; Terrence W. Doyle, Fayetteville, N.Y.

[73] Assignee: Bristol-Myers Company, New York, N.Y.

[*] Notice: The portion of the term of this patent subsequent to Sep. 1, 2004 has been disclaimed.

[21] Appl. No.: 781,076

[22] Filed: Sep. 23, 1985

Related U.S. Application Data

[63] Continuation-in-part of Ser. No. 581,291, Feb. 24, 1984, Pat. No. 4,803,212, which is a continuation-in-part of Ser. No. 484,016, Apr. 12, 1983, abandoned.

[51] Int. Cl.$^4$ ............... C07D 487/14; A61K 31/40
[52] U.S. Cl. .................................. 546/271; 548/422
[58] Field of Search ..................... 548/422; 546/271

[56] References Cited

U.S. PATENT DOCUMENTS

| | | | |
|---|---|---|---|
| 3,332,944 | 7/1967 | Cosulich et al. | 548/422 |
| 3,420,846 | 1/1969 | Matsui et al. | 260/295 |
| 3,450,705 | 6/1969 | Matsui et al. | 260/295 |
| 3,514,452 | 5/1970 | Matsui et al. | 260/240 |
| 3,660,578 | 5/1972 | Hata et al. | 424/274 |
| 4,231,936 | 11/1980 | Nakano et al. | 260/326.24 |
| 4,268,676 | 5/1981 | Remers | 548/181 |
| 4,691,024 | 9/1987 | Shirahata et al. | 548/422 |

FOREIGN PATENT DOCUMENTS

| | | |
|---|---|---|
| 892162 | 5/1982 | Belgium . |
| 0116208 | 8/1984 | European Pat. Off. . |
| 0163550 | 12/1985 | European Pat. Off. . |

OTHER PUBLICATIONS

March, *Advanced Organic Chemistry*, 2nd ed. (1977), p. 1115.
J. Amer. Chem. Soc. 84, 3185–3187 (1962), J. S. Webb et al.
The Journal of Antibiotics, XXI, 189–198 (1968), Matsui et al.
J. Med. Chem. 14, 103–109 (1971), Kinoshita et al.
J. Med. Chem. 24, 975–981 (1981), Iyengar et al.
Physicians' Desk Reference, 35th Edition, 1981, pp. 717–718.
Iyengar et al.—Abstracts of Papers, 183rd Annual Meeting of the American Chemical Society, Mar. 1982, No. MEDI 72.
C. A. Claridge et al.—Abst. of the Annual Meeting of Amer. Soc. for Microbiology, 1982, Abs. 028.
J. Med. Chem., 1983, 26, 16–20, Iyengar et al.
Iyengar et al., Abstracts of Papers, 185th Annual Meeting of the American Chemical Society, Mar. 1983, No. MEDI 82.
Farmdoc No. 56227 D/31.
American Association of Cancer Research Poster Material presented May 25, 1983 in San Diego, Calif.
Shirahata et al., J. Am. Chem. Soc., 1983, 105, 7199–7200.

*Primary Examiner*—Nicholas S. Rizzo
*Attorney, Agent, or Firm*—Robert E. Carnahan

[57] ABSTRACT

This invention refers to 7-amino mitosane analogs (mitomycin C) in which the 7-amino group bears an organic substituent incorporating a disulfide group and to a novel thiol exchange process for producing these compounds. The compounds are inhibitors of experimental animal tumors.

38 Claims, No Drawings

AMINO DISULFIDE THIOL EXCHANGE PRODUCTS

REFERENCE TO RELATED APPLICATIONS

This application is a continuation-in-part of application U.S. Ser. No. 581,291 filed Feb. 24, 1984 now Pat. No. 4,803,212 which in turn is a continuation-in-part of Ser. No. 484,016 filed Apr. 12, 1983, and now abandoned. The entire disclosure of U.S. Ser. No. 581,291 is incorporated herein by reference.

FIELD OF THE INVENTION

The present compounds are mitomycin C analogs (Class 548, Subclass 422) in which the 7-amino group is substituted by a disulfide containing organic group. These compounds are inhibitors of experimental animal tumors.

BACKGROUND OF THE INVENTION

Nomenclature—The systematic Chemical Abstracts name for mitomycin C is (Shirahata et al., J. Am. Chem. Soc. 1983, 105, 7199-7200):
[1aS-(1aβ,8β,8aα,8β)]-6-amino-8-[(aminocarbonyl)oxy)methyl]-1,1a,2,8,8a,8b-hexahydo-8a-methoxy-5-methylarizidino[2′,3′,3,4,]pyrrolo[1,2-a]indole-4,7-dione according to which the azirinopyrroloindole ring system is numbered as follows:

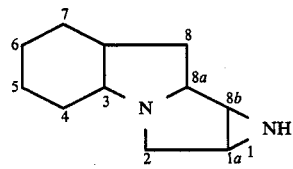

Chemical Abstracts

A trivial system of nomenclature which has found wide use in the mitomycin literature identifies the foregoing ring system including several of the characteristic substituents of the mitomycins as mitosane.

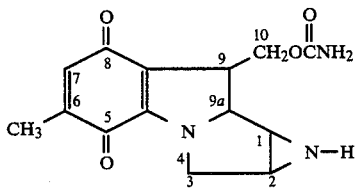

Mitosane

We have chosen in the present specification to use this system and to refer to the aziridino nitrogen atom as 1a and the ring amino nitrogen atom as 7-$NH_2$. As to the stereochemical configuration of the products of this invention, it is intended when identifying them by the root name "mitosane" or by structural formula to identify the stereochemical configuration thereof as the same as that of mitomycin C.

DESCRIPTION OF THE PRIOR ART

Mitomycin C is an antibiotic which is produced by fermentation and is presently on sale under Food and Drug Administration approval for the therapy of disseminated adenocarcinoma of the stomach or pancreas in proven combinations with other approved chemotherapeutic agents and as palliative teatment when other modalities have failed (Mutamycin® Bristol Laboratories, Syracuse, N.Y. 13201, Physicians' Desk Reference 35th Edition, 1981, pp. 717 and 718). Mitomycin C and its production by fermentation is the subject of U.S. Pat. No. 3,660,578 patented May 2, 1972 claiming priority from earlier applications including an application filed in Japan on Apr. 6, 1957.

The structures of mitomycins A, B, C, and of porfiromycin were first published by J. S. Webb et al. of Lederle Laboratories Division American Cyanamid Company, J. Amer. Chem. Soc. 84, 3185-3187 (1962). One of the chemical transformations used in this structure study to relate mitomycin A and mitomycin C was the conversion of the former, 7-9α-dimethoxymitosane, by reaction with ammonia to the latter, 7-amino-9α-methoxymitosane. Displacement of the 7-methoxy group of mitomycin A has proven to be a reaction of considerable interest in the preparation of antitumor active derivatives of mitomycin C. The following articles and patents deal with the conversion of mitomycin A to 7-substituted amino mitomycin C derivatives having antitumor activity. The object of this research was to prepare derivatives which were more active, and particularly which were less toxic than mitomycin C:

Matsui et al. The Journal of Antibiotics, XXI, 189-198 (1968).

Kinoshita et al. J. Med. Chem. 14, 103-109 (1971).

Iyengar et al. J. Med. Chem. 24, 975-981 (1981).

Iyengar, Sami, Remers, and Bradner, Abstracts of Papers 183rd Annual Meeting of the American Chemical Society, March 1982, No. MEDI 72.

Iyengar et al. J. Med. Chem. 1983, 26, 16-20.

Iyengar et al. Abstracts of Papers, 185th Annual Meeting of the American Chemical Society, March 1983, No. MEDI 82.

The following patents deal with the preparation of 7-substituted aminomitosane derivatives by the reaction of mitomycin A, mitomycin B, or an $N^{1a}$-substituted derivative thereof with a primary or secondary amine:

Cosulich et al. U.S. Pat. No. 3,332,944 patented July 25, 1967.

Matsui et al. U.S. Pat. No. 3,420,846 patented Jan. 7, 1969.

Matsui et al. U.S. Pat. No. 3,450,705 patented June 17, 1969.

Matsui et al. U.S. Pat. No. 3,514,452 patented May 26, 1970.

Nakano et al. U.S. Pat. No. 4,231,936 patented Nov. 4, 1980.

Remers, U.S. Pat. No. 4,268,676 patented May 19, 1981.

Remers, Belg. No. 893,162 patented May 12, 1982.

Mitomycin C derivatives having a substituted amino substituent in the 7-position have also been prepared by directed biosynthesis, that is by supplementing fermentation broths with a series of primary amines, and carrying out the conventional mitomycin fermentation (C. A. Claridge et al. Abst. of the Annual Meeting of Amer. Soc. for Microbiology 1982. Abs. 028).

SUMMARY OF THE INVENTION

The present invention relates to a process for the preparation of the compounds claimed in U.S. Ser. No. 581,291 which are represented by Formula IX below. The process is depicted in the reaction scheme shown.

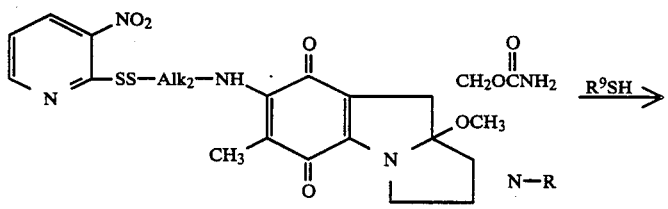

Compound No. 30

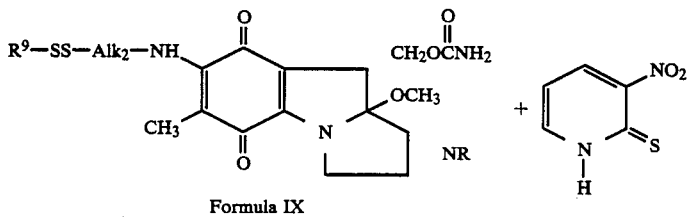

Formula IX

In Formula IX $R^9$ is an organic group, viz. the structural component of an organic thiol of the Formula $R^9SH$. R and $Alk_2$ have the definitions given in U.S. Ser. No. 581,291 viz. R is hydrogen, lower alkyl, lower alkanoyl, benzoyl, or substituted benzoyl wherein said substituent is lower alkyl, lower alkoxy, halo, amino, or nitro. $Alk_2$ is a straight or branched chain alkylene group having 2 to 7 carbon atoms and optionally bearing an $R^7$ substituent wherein said $R^7$ is selected from the group consisting of hydroxy, halo, amino, alkylamino or dialkylamino having 1 to 12 atoms, alkanoylamino, benzoylamino or A-substituted benzoylamino, naphthoylamino or A-substituted naphthoylamino, cycloalkyl or A-substituted cycloalkyl each having 3 to 8 members, cycloalkenyl or A-substituted cycloalkenyl each having 5 to 8 ring members, phenyl or A-substituted phenyl, naphthyl or A-substituted naphthyl, a heterocyclic group selected from the group consisting of heteroaromatic and heteroalicyclic groups having from 1 to 2 rings, from 3 to 8 ring members in each ring, and from 1 to 4 hetero atoms selected from oxygen, nitrogen, and sulfur, alkoxy or alkythio each having 1 to 6 carbon atoms, carboxy, alkoxycarbonyl having 1 to 7 carbon atoms, phenoxycarbonyl or A-substituted phenoxy, naphthoxy or A-substituted naphthoxy, alkoxycarbonylamino having 2 to 6 carbon atoms, guanidino, ureido (—$NHCONH_2$), N-alkylureylene (—NHCONHalkyl) having 2 to 7 carbon atoms, $N^3$-haloalkylureylene having 3 to 7 carbon atoms, $N^3$-haloalkyl-$N^3$-nitrosoureylene having 3 to 7 carbon atoms, and dialkylaminocarbonyl having 3 to 13 carbon atoms, wherein said A substituent is selected from the group consisting of one or two lower alkyl, lower alkanoyl, lower alkoxy, halo, amino, hydroxy, or nitro groups. The entire disclosure of U.S. Ser. No. 581,291 is incorporated herein by reference.

In the operation of the present process a number of novel compounds of Formula IX have been produced. These compounds have antitumor activity and inhibit the growth of experimental animal tumors. They are considered part of the present invention.

DETAILED DESCRIPTION OF THE INVENTION

The reagent employed in the present process in reaction with thiols of the Formula $R^9SH$ is referred to as Compound No. 30. The preparation thereof is described in U.S. Ser. No. 581,291 in Procedure No. 30 where it is also referred to as Compound No. 30. This is a particularly preferred reactant because of the stability of the by-product 3-nitro-2-pyridyldthione which is produced in the process and which is believed to provide a driving force for completion of the reaction. A similar disulfide thiol exchange process has been described by Kono et al. in European Patent Application Publication No. 0116208 published Aug. 22, 1984. In that process the 2-pyridylsulfide corresponding in structure to Compound No. 30 is employed. 3-Nitro-1-pyridylthione is a more facile leaving group, and as a result the present process enjoys certain advantages over that process.

The process as described in the above reaction scheme takes place at a temperature in the range of 0 to 60 deg. C., the particular temperature being chosen on the basis of the reactivity of the thiol and the stability of the product produced. The reaction is carried out in a reaction inert liquid medium preferably one in which the reactants are soluble. At least one chemical equivalent of the thiol $R^9SH$ relative to Compound 30 is employed. It is preferable to carry out the reaction in the presence of a base such as a tertiary amine. With water-soluble thiol reactants, water may be used as the reaction inert liquid medium and sodium bicarbonate is preferred as the base. Approximately one chemical equivalent of base per quantity of Compound 30 is employed. Suitable reaction inert liquid media include lower alkanols, such as methanol, ethanol, and isopropanol, lower alkanoic lower alkyl esters such as ethyl acetate, methyl propionate, and butyl acetate may be employed. Other appropriate reaction media include lower aliphatic ketones such as acetone and methylethyl ketone, cyclic aliphatic ethers such as tetrahydrofuran and lower polyhalogenated aliphatic hydrocarbons such as methylene chloride, ethylene dichloride, and chloroform.

DESCRIPTION OF SPECIFIC EMBODIMENTS

In the following procedures and examples, all temperatures are given in degrees centigrade, and melting points are uncorrected. Proton nuclear magnetic resonance ($^1H$ NMR) spectra were recorded on Joel FX-90Q or Bunker VM 360 spectrometer in either pyridine-$d_5$ or $D_2O$ as indicated. When pyridine-$d_5$ was used as the solvent, the pyridine resonance at 8.57 PPM was used as an internal reference, whereas with $D_2O$ as solvent trimethylsilylpropane sulfonic acid (TSP) was used as the internal reference. Chemical shifts are reported in parts per million (PPM), and integrals proportional to the areas under each shift are reported. Where splitting patterns are given, the following abbreviations are used: s, singlet; d, doublet; t, triplet; q, quartet; m, multiplet; bs, broad singlet; dd, double of doublets; dt, doublet of triplets. Where they are not given, the data presented are sufficient to provide such analysis if desired. Infrared spectra (IR) were determined either on a Beckman Model 4240 spectrometer or a Nicolet 5DX FT-IR spectrometer and are reported in reciprocal centimeters. Ultraviolet (UV) spectra were determined either on a Cary Model 290 spectrometer or a Hewlitt Packard 8450A spectrometer equipped with a multidiode array detector. Thin layer chromatography (TLC) was carried out on 0.25 mm Analtech silica gel GF plates or Whatmann MK6F silica gel plates. Flash chromatography was run with either Woelm neutral alumina (DCC grade) or Woelm silica gel (32–63 μm) and the indicated solvents. Reverse phase high pressure liquid chromatography (HLPC) was performed on μ Bondpack-$C_{18}$ column using Waters 6000 pump which is equipped with a Waters 440 UV detector. Reverse phase column chromatography was performed using C-18 silica gel in solvents indicated. All evaporations of solvents were performed under reduced pressure and below 40 eg. C.

The process was applied in one of two procedures using various thiols as reactant with 7-[2-(3-nitro-2-pyridyldithio)ethylamino]-9a-methoxymitosane. The latter has been previously described in application Ser. No. 581,291 filed Feb. 24, 1984 and its preparation more particularly below.

7-[2-(3-Nitro-2-pyridyldithio)ethylamino]-9a-methoxymitosane

To a solution of 7-dimethylaminomethyleneamino-9a-methoxymitosane (1.0 g, 2.61 mM) in deoxygenated methanol (15 ml) was added triethylamine (1.1 ml, 7.83 mM) under stirring and ice bath temperature (0 deg. ca. 4 deg. C.). The reaction mixture was sonicated and allowed to stir at ca. 22 deg. C. for 24 hours. Thin layer chromatography (silica gel, 10% $CH_3OH$ in $CH_2Cl_2$) revealed that >90% of the starting compound (green) had been converted to the desired blue compound. The reaction mixture was concentrated under reduced pressure and the resulting residue was chromatographed on 1"×16" column packet with silica gel in 5% MeOH in $CH_2Cl_2$. Gradient elution with MeOH, 1–5% v/v in $CH_2Cl_2$ afforded the title compound as a pure bluish amorphous solid (430 mg). The spectral properties of this material are in agreement with those reported in U.S. Ser. No. 582,291.

Method A—Preferred For Lipophilic Products

To a deoxygenated solution of 7-[2-(3-nitro-2-pyridyldithio)ethylamino]-9a-methoxymitosane (ca. 1.1 equiv.) in acetone (3–5 ml) is added with stirring, under an argon or nitrogen atmosphere, triethylamine (ca. 1.1 equiv.) followed by dropwise or portionwise addition of the thiol reactant (1 equiv.) in acetone (1–2 ml). The progress of the reaction is monitored by silica gel thin layer chromatography (10% MeOH in $CH_2Cl_2$), unless the starting nitropyridyldithio mitosane reactant and the product have similar Rf values. In such instances HPLC monitoring is employed (μ Bondpack-$C_{18}$). The completion of the reaction is apparent when disappearance of the reactant and appearance of the product occurs. At this point the reaction mixture is concentrated under reduced pressure (ca. 30 deg. C.) and the residue chromatographed on a neutral Woelm alumina column (¼×10") packed employing 2–5% MeOH in $CH_2Cl_2$ for slurrying. This procedure separates the desired mitosane product from the pyridyl thione by-product which remains on the column. The product thus eluted using 2% MeOH in $CH_2Cl_2$ is further purified by flash silica gel chromatography using 5–7%. MeOH in $CH_2Cl_2$ as the eluting solvent. The major band corresponding to product is isolated and the amorphous product characterized.

Examples 1–25 employ method A applied to various neutral lipophilic thiols or those containing basic groups.

Method B—Preferred for Hydrophilic Products

To solution of 7-[2-(3-nitro-2-pyridyldithio)ethylamino]-9a-methoxymitosane (ca. 0.1 mM) in methanol (10 ml) containing 2–5% v/v of acetone (or 2–5% v/v methylene chloride) is added sat. aq. $NaHCO_3$ solution (6 drops), and a methanolic solution of 1 chemical equivalent of the thiol, volume ca. 1 ml water may be used as solvent for the thiol if the water solubility thereof is sufficient. The progress of the reaction is monitored by thin layer chromatography (silica gel, 10% MeOH in $CH_2Cl_2$). At the completion of reaction, the reaction mixture is diluted with water (15 ml) and concentrated to ca. 10 ml on a rotavapor at 30 deg. C. The resulting solution is chromatographed on a reverse phase C-18 column with stepwise gradient elution (100% $H_2O$ to 80% MeOH in $H_2O$). The product is eluted after elution of the by-product thione at the increased methanol concentrations. The product appears as a major blue fraction, which is collected, and concentrated to yield an amorphous solid. If further purification is needed the above chromatograph step is repeated.

Examples 26–30 employ Method B applied to various thiols containing salt-forming groups.

EXAMPLE 1

7-[2-(4-Chlorophenyldithio)ethylamino]-9a-methoxymitosane (39).—Method A employing 4-chlorothiophenol $^1H$ NMR data (pyridine $d_5$):

| FREQUENCY | PPM | INTEGRAL |
|---|---|---|
| 3143.874 | 8.7297 | .718 |
| 2739.107 | 7.6058 | .111 |
| 2729.688 | 7.5796 | 1.052 |
| 2721.412 | 7.5567 | .593 |
| 2718.682 | 7.5491 | .097 |
| 2669.282 | 7.4119 | .585 |
| 2667.385 | 7.4066 | .108 |
| 2662.528 | 7.3932 | .118 |
| 2660.613 | 7.3878 | .367 |
| 2650.480 | 7.3597 | .064 |
| 2608.945 | 7.2444 | .184 |
| 2602.620 | 7.2268 | .282 |
| 2596.156 | 7.2089 | .984 |
| 1954.657 | 5.4276 | .189 |
| 1950.505 | 5.4161 | .144 |
| 1944.312 | 5.3989 | .170 |
| 1940.091 | 5.3871 | .164 |
| 1847.791 | 5.1308 | .203 |
| 1837.219 | 5.1015 | .271 |
| 1826.720 | 5.0723 | .180 |
| 1774.500 | 4.9273 | 2.884 |

-continued

| FREQUENCY | PPM | INTEGRAL |
|---|---|---|
| 1637.494 | 4.5469 | .337 |
| 1624.753 | 4.5115 | .334 |
| 1452.696 | 4.0338 | .168 |
| 1448.520 | 4.0222 | .172 |
| 1441.467 | 4.0026 | .171 |
| 1437.340 | 3.9911 | .157 |
| 1404.385 | 3.8996 | .221 |
| 1397.740 | 3.8812 | .455 |
| 1391.049 | 3.8626 | .454 |
| 1384.386 | 3.8441 | .196 |
| 1302.465 | 3.6166 | .351 |
| 1290.130 | 3.5824 | .268 |
| 1178.026 | 3.2711 | .077 |
| 1164.985 | 3.2349 | 1.850 |
| 1134.073 | 3.1490 | .626 |
| 1095.041 | 3.0406 | .390 |
| 1088.318 | 3.0220 | .608 |
| 1081.611 | 3.0034 | .307 |
| 992.057 | 2.7547 | .684 |
| 772.470 | 2.1450 | .197 |
| 766.114 | 2.1273 | .340 |
| 734.164 | 2.0386 | 1.886 |
| −.000 | −.0000 | 2.063 |

IR (KBr, $\nu_{max}$, cm$^{-1}$): 3440, 3280, 2950, 1720, 1635, 1560, 1510, 1474, 1450, 1325, 1060.

UV (MeOH, $\lambda_{max}$, nm): 368, 238(sh), 220.

EXAMPLE 2

7-[2-(4-Bromophenyldithio)ethylamino]-9a-methoxymitosane (47).—Method A employing 4-bromothiophenol $^1$H NMR data (pyridine d$_5$):

| FREQUENCY | PPM | INTENSITY |
|---|---|---|
| 3086.651 | 8.5709 | 89.671 |
| 2692.567 | 7.4766 | 1.360 |
| 2670.818 | 7.4162 | 68.621 |
| 2659.543 | 7.3849 | 6.161 |
| 2657.684 | 7.3797 | 16.591 |
| 2648.749 | 7.3549 | 17.557 |
| 2641.944 | 7.3360 | 4.239 |
| 2639.909 | 7.3304 | 8.364 |
| 2638.621 | 7.3268 | 9.969 |
| 2626.614 | 7.2935 | 2.401 |
| 2624.367 | 7.2872 | 7.673 |
| 2617.778 | 7.2689 | 2.270 |
| 2615.699 | 7.2632 | 4.312 |
| 2587.041 | 7.1836 | 1.322 |
| 2582.594 | 7.1712 | 1.049 |
| 2578.892 | 7.1610 | 1.083 |
| 2551.216 | 7.0841 | 3.986 |
| 2538.742 | 7.0495 | 81.002 |
| 1898.031 | 5.2704 | 2.688 |
| 1893.978 | 5.2591 | 2.499 |
| 1887.686 | 5.2417 | 3.413 |
| 1883.492 | 5.2300 | 2.797 |
| 1778.104 | 4.9374 | 1.283 |
| 1727.439 | 4.7967 | 13.889 |
| 1581.651 | 4.3919 | 4.812 |
| 1575.060 | 4.3736 | 1.534 |
| 1568.837 | 4.3563 | 4.992 |
| 1395.824 | 3.8759 | 2.829 |
| 1391.542 | 3.8640 | 2.931 |
| 1384.700 | 3.8450 | 3.059 |
| 1380.440 | 3.8332 | 2.521 |
| 1345.894 | 3.7372 | 2.265 |
| 1339.257 | 2.7188 | 6.127 |
| 1332.587 | 3.7003 | 6.513 |
| 1325.939 | 3.6818 | 2.754 |
| 1247.979 | 3.4653 | 1.699 |
| 1235.355 | 3.4303 | 1.647 |
| 1109.433 | 3.0806 | 12.799 |
| 1107.467 | 3.0752 | 43.984 |
| 1097.943 | 3.0487 | 1.301 |
| 1090.735 | 3.0287 | 1.284 |
| 1084.521 | 3.0115 | 2.465 |
| 1078.013 | 2.9934 | 2.825 |
| 1035.937 | 2.8765 | 4.635 |
| 1029.085 | 2.8575 | 8.015 |
| 1022.373 | 2.8389 | 4.583 |
| 934.207 | 2.5941 | 2.907 |
| 920.895 | 2.5571 | 2.572 |
| 715.422 | 1.9866 | 1.426 |
| 676.497 | 1,8785 | 29.005 |

EXAMPLE 3

7-[2-(4-Fluorophenyldithio)ethylamino]-9a-methoxymitosane (46).—Method A employing 4-fluorothiophenol $^1$H NMR data (pyridine d$_5$):

| FREQUENCY | PPM | INTENSITY |
|---|---|---|
| 3094.793 | 8.5935 | 2.949 |
| 3086.092 | 8.5693 | 71.400 |
| 2692.617 | 7.4767 | 3.235 |
| 2687.390 | 7.4622 | 3.980 |
| 2684.098 | 7.4531 | 4.265 |
| 2678.931 | 7.4387 | 5.898 |
| 2670.028 | 7.4140 | 53.786 |
| 2547.257 | 7.0731 | 3.842 |
| 2538.009 | 7.0474 | 68.631 |
| 2523.997 | 7.0085 | 7.543 |
| 2515.342 | 6.9845 | 3.861 |
| 1897.552 | 5.2690 | 1.499 |
| 1893.349 | 5.2574 | 1.623 |
| 1887.153 | 5.2401 | 1.938 |
| 1883.067 | 5.2288 | 1.801 |
| 1779.560 | 4.9414 | 1.318 |
| 1722.527 | 4.7830 | 12.566 |
| 1578.645 | 4.3835 | 2.931 |
| 1565.979 | 4.3483 | 3.234 |
| 1394.123 | 3.8711 | 1.739 |
| 1389.902 | 3.8594 | 2.078 |
| 1382.885 | 3.8399 | 1.855 |
| 1378.856 | 3.8287 | 1.706 |
| 1351.510 | 3.7528 | 1.469 |
| 1344.836 | 3.7343 | 4.057 |
| 1338.216 | 3.7159 | 4.463 |
| 1331.635 | 3.6976 | 2.077 |
| 1244.124 | 3.4546 | 1.293 |
| 1231.741 | 3.4202 | 1.222 |
| 1106.270 | 3.0718 | 21.973 |
| 1083.640 | 3.0090 | 1.398 |
| 1077.831 | 2.9929 | 1.653 |
| 1039.104 | 2.8853 | 3.199 |
| 1032.385 | 2.8667 | 5.933 |
| 1025.696 | 2.8481 | 3.204 |
| 932.666 | 2.5898 | 1.743 |
| 711.666 | 1.9761 | 1.244 |
| 693.178 | 1.9248 | 1.762 |
| 679.305 | 1.8863 | 16.668 |

IR (KBr, $\nu_{max}$, cm$^{-1}$): 3430, 3290, 2920, 1720, 1640, 1560, 1510, 1450, 1330, 1220, 1060.

UV (MeOH, $\lambda_{max}$, nm): 370, 222.

EXAMPLE 4

7-[2-(2-Chlorophenyldithio)ethylamino]-9a-methoxymitosane (55).—Method A employing 2-chlorothiophenol $^1$H NMR data (pyridine d$_5$):

| FREQUENCY | PPM | INTENSITY |
|---|---|---|
| 3086.658 | 8.5709 | 354.920 |

| FREQUENCY | PPM | INTENSITY |
|---|---|---|
| 2789.230 | 7.7450 | 3.788 |
| 2781.178 | 7.7226 | 3.903 |
| 2670.412 | 7.4151 | 203.198 |
| 2637.641 | 7.3241 | 1.251 |
| 2619.047 | 7.2724 | 2.538 |
| 2608.912 | 7.2443 | 4.008 |
| 2601.011 | 7.2224 | 4.991 |
| 2589.766 | 7.1911 | 4.802 |
| 2582.103 | 7.1699 | 2.684 |
| 2538.357 | 7.0484 | 328.954 |
| 2523.173 | 7.0062 | 5.084 |
| 2515.145 | 6.9839 | 2.755 |
| 1896.130 | 5.2651 | 1.917 |
| 1891.886 | 5.2533 | 2.057 |
| 1885.611 | 5.2359 | 2.262 |
| 1881.627 | 5.2248 | 2.601 |
| 1778.080 | 4.9373 | 1.120 |
| 1730.238 | 4.8044 | 7.522 |
| 1574.972 | 4.3733 | 3.765 |
| 1562.242 | 4.3380 | 4.063 |
| 1392.854 | 3.8676 | 2.196 |
| 1388.576 | 3.8557 | 2.054 |
| 1381.591 | 3.8363 | 2.036 |
| 1377.677 | 3.8255 | 1.722 |
| 1349.813 | 3.7481 | 1.665 |
| 1342.946 | 3.7290 | 4.142 |
| 1336.349 | 3.7107 | 4.217 |
| 1329.647 | 3.6921 | 1.963 |
| 1245.714 | 3.4590 | 1.625 |
| 1234.390 | 3.4276 | 1.448 |
| 1104.953 | 3.0682 | 28.534 |
| 1074.486 | 2.9836 | 2.319 |
| 1031.569 | 2.8644 | 3.910 |
| 1024.929 | 2.8460 | 7.145 |
| 1018.285 | 2.8275 | 3.493 |
| 932.398 | 2.5890 | 2.552 |
| 814.080 | 2.2605 | 1.350 |
| 723.808 | 2.0098 | 1.102 |
| 677.286 | 1.8807 | 23.661 |

EXAMPLE 5

7-[2-(2-Bromophenyldithio)ethylamino]-9a-methoxymitosane (65).—Method A employing 2-bromothiophenyl $^1$H NMR data (pyridine $d_5$):

| FREQUENCY | PPM | INTENSITY |
|---|---|---|
| 3088.884 | 8.5771 | 89.791 |
| 2790.861 | 7.7495 | 1.858 |
| 2783.064 | 7.7279 | 1.813 |
| 2673.036 | 7.4223 | 53.965 |
| 2664.964 | 7.3999 | 2.421 |
| 2618.223 | 7.2701 | 1.113 |
| 2610.639 | 7.2491 | 1.762 |
| 2602.928 | 7.2277 | 1.102 |
| 2541.000 | 7.0557 | 85.566 |
| 2503.916 | 6.9527 | 1.066 |
| 2496.358 | 6.9318 | 1.634 |
| 1897.870 | 5.2699 | 1.013 |
| 1893.745 | 5.2585 | 1.002 |
| 1887.532 | 5.2412 | 1.121 |
| 1883.415 | 5.2298 | 1.057 |
| 1786.096 | 4.9595 | .967 |
| 1722.377 | 4.7826 | 6.918 |
| 1576.483 | 4.3775 | 1.624 |
| 1563.921 | 4.3426 | 1.608 |
| 1394.999 | 3.8736 | 1.179 |
| 1390.756 | 3.8618 | 1.250 |
| 1383.913 | 3.8428 | 1.122 |
| 1379.766 | 3.8313 | .993 |
| 1344.182 | 3.7325 | 2.005 |
| 1337.507 | 3.7139 | 2.071 |
| 1330.434 | 3.6943 | .886 |
| 1246.383 | 3.4609 | 1.448 |
| 1233.693 | 3.4257 | .868 |
| 1107.612 | 3.0756 | 13.542 |
| 1079.502 | 2.9975 | 1.012 |
| 1033.690 | 2.8703 | 1.964 |
| 1026.784 | 2.8511 | 3.463 |
| 1020.295 | 2.8331 | 1.614 |
| 934.405 | 2.5946 | 1.081 |
| 712.878 | 1.9795 | .946 |
| 680.366 | 1.8892 | 8.887 |

EXAMPLE 6

7-[2-(2,6-Dichlorophenyldithio)ethylamino]-9a-methoxymitosane (52).—Method A employing 2,6-dichlorothiophenol $^1$H NMR data (pyridine $d_5$):

| FREQUENCY | PPM | INTENSITY |
|---|---|---|
| 3096.025 | 8.5969 | 8.989 |
| 3086.614 | 8.5707 | 262.213 |
| 2757.647 | 7.6573 | 1.502 |
| 2749.367 | 7.6343 | 2.218 |
| 2681.319 | 7.4453 | 6.546 |
| 2670.136 | 7.4143 | 186.273 |
| 2628.286 | 7.2981 | 6.863 |
| 2620.169 | 7.2755 | 9.717 |
| 2609.009 | 7.2446 | 5.966 |
| 2600.963 | 7.2222 | 7.438 |
| 2588.248 | 7.1869 | 2.117 |
| 2575.576 | 7.1517 | 2.086 |
| 2547.255 | 7.0731 | 10.360 |
| 2538.154 | 7.0478 | 246.987 |
| 2480.023 | 6.8864 | 2.321 |
| 2456.668 | 6.8215 | 1.852 |
| 1887.908 | 5.2422 | 2.396 |
| 1883.629 | 5.2304 | 2.872 |
| 1877.625 | 5.2137 | 2.760 |
| 1873.527 | 5.2023 | 2.333 |
| 1769.319 | 4.9130 | 1.869 |
| 1731.124 | 4.8069 | 27.138 |
| 1574.128 | 4.3710 | 3.646 |
| 1568.549 | 4.3555 | 2.207 |
| 1561.432 | 4.3357 | 3.744 |
| 1393.054 | 3.8682 | 1.600 |
| 1378.772 | 3.8285 | 5.597 |
| 1371.943 | 3.8095 | 5.806 |
| 1247.970 | 3.4653 | 2.467 |
| 1234.722 | 3.4285 | 2.453 |
| 1106.516 | 3.0725 | 5.404 |
| 1102.314 | 3.0608 | 31.217 |
| 1084.696 | 3.0119 | 2.885 |
| 1078.844 | 2.9957 | 5.611 |
| 1073.435 | 2.9807 | 7.611 |
| 1059.705 | 2.9425 | 1.695 |
| 1029.741 | 2.8593 | 1.906 |
| 1022.765 | 2.8400 | 2.499 |
| 931.917 | 2.5877 | 3.399 |
| 920.768 | 2.5567 | 3.018 |
| 715.360 | 1.9864 | 7.831 |
| 694.846 | 1.9294 | 20.393 |
| 680.187 | 1.8887 | 2.738 |

EXAMPLE 7

7-[2-(2,4-Dichlorophenyldithio)ethylamino]-9a-methoxymitosane (50).—Method A employing 2,4-dichlorothiophenol $^1$H NMR data (pyridine $d_5$):

| FREQUENCY | PPM | INTENSITY |
|---|---|---|
| 3104.914 | 8.6216 | 1.922 |
| 3095.765 | 8.5962 | 4.052 |
| 3086.609 | 8.5707 | 182.092 |

| FREQUENCY | PPM | INTENSITY |
|---|---|---|
| 2757.604 | 7.6572 | 5.758 |
| 2748.941 | 7.6331 | 6.143 |
| 2680.773 | 7.4438 | 2.431 |
| 2670.316 | 7.4148 | 91.168 |
| 2649.396 | 7.3567 | 2.942 |
| 2647.244 | 7.3507 | 3.044 |
| 2642.923 | 7.3387 | 4.735 |
| 2640.803 | 7.3328 | 5.330 |
| 2618.698 | 7.2715 | 1.614 |
| 2614.924 | 7.2610 | 3.814 |
| 2612.799 | 7.2551 | 3.410 |
| 2606.232 | 7.2369 | 2.780 |
| 2604.107 | 7.2310 | 2.635 |
| 2581.846 | 7.1691 | 2.391 |
| 2579.685 | 7.1631 | 2.306 |
| 2573.061 | 7.1447 | 2.746 |
| 2571.061 | 7.1392 | 2.537 |
| 2565.809 | 7.1246 | 2.759 |
| 2557.328 | 7.1011 | 2.389 |
| 2549.032 | 7.0780 | 3.230 |
| 2538.315 | 7.0483 | 160.796 |
| 1897.970 | 5.2702 | 2.212 |
| 1893.650 | 5.2582 | 2.722 |
| 1887.692 | 5.2416 | 2.893 |
| 1883.310 | 5.2295 | 3.084 |
| 1732.330 | 4.8102 | 7.576 |
| 1578.543 | 4.3832 | 3.968 |
| 1565.749 | 4.3477 | 4.456 |
| 1395.962 | 3.8762 | 2.544 |
| 1391.700 | 3.8644 | 2.705 |
| 1384.733 | 3.8451 | 2.783 |
| 1380.505 | 3.8333 | 2.495 |
| 1353.560 | 3.7585 | 1.798 |
| 1346.688 | 3.7394 | 4.196 |
| 1339.996 | 3.7208 | 4.343 |
| 1333.396 | 3.7025 | 2.176 |
| 1247.381 | 3.4637 | 2.113 |
| 1234.770 | 3.4286 | 1.996 |
| 1106.762 | 3.0732 | 30.694 |
| 1103.861 | 3.0651 | 9.733 |
| 1097.728 | 3.0481 | 1.741 |
| 1072.702 | 2.9786 | 2.531 |
| 1037.593 | 2.8811 | 3.372 |
| 1030.795 | 2.8623 | 6.451 |
| 1023.941 | 2.8432 | 4.061 |
| 932.000 | 2.5879 | 2.626 |
| 715.409 | 1.9865 | 5.066 |
| 680.055 | 1.8883 | 20.943 |

EXAMPLE 8

7-[2-(3-Chlorophenyldithio)ethylamino]-9a-methoxymitosane (58).—Method A employing 3-chlorothiophenol $^1$H NMR data (pyridine d$_5$):

| FREQUENCY | PPM | INTENSITY |
|---|---|---|
| 3085.348 | 8.5672 | 71.364 |
| 2713.519 | 7.5348 | 4.491 |
| 2669.389 | 7.4122 | 42.733 |
| 2641.517 | 7.3348 | 2.420 |
| 2635.412 | 7.3179 | 2.638 |
| 2617.780 | 7.2689 | 1.198 |
| 2571.300 | 7.1399 | 2.474 |
| 2563.321 | 7.1177 | 5.302 |
| 2557.187 | 7.1007 | 8.024 |
| 2537.316 | 7.0455 | 69.130 |
| 1894.009 | 5.2592 | 1.711 |
| 1889.794 | 5.2475 | 1.805 |
| 1883.499 | 5.2300 | 1.907 |
| 1879.433 | 5.2187 | 1.777 |
| 1778.965 | 4.9397 | 1.352 |
| 1724.502 | 4.7885 | 3.265 |
| 1575.192 | 4.3739 | 2.862 |
| 1562.650 | 4.3391 | 2.779 |
| 1392.023 | 3.8653 | 1.811 |
| 1387.906 | 3.8539 | 1.948 |
| 1381.000 | 3.8347 | 1.955 |
| 1376.859 | 3.8232 | 1.666 |
| 1344.147 | 3.7324 | 1.781 |
| 1337.633 | 3.7143 | 3.485 |
| 1331.146 | 3.6963 | 3.485 |
| 1324.709 | 3.6784 | 1.715 |
| 1243.697 | 3.4534 | 1.365 |
| 1231.901 | 3.4207 | 1.357 |
| 1104.883 | 3.0680 | 17.210 |
| 1073.619 | 2.9812 | 1.880 |
| 1033.597 | 2.8700 | 3.316 |
| 1026.901 | 2.8514 | 5.149 |
| 1020.257 | 2.8330 | 2.821 |
| 932.403 | 2.5890 | 2.072 |
| 710.311 | 1.9724 | 1.386 |
| 692.134 | 1.9219 | 1.843 |
| 674.921 | 1.8741 | 14.080 |

EXAMPLE 9

7-[2-(2,5-Dichlorophenyldithio)ethylamino]-9a-methoxymitosane (57).—Method A employing 2,5-dichlorothiophenol $^1$H NMR data (pyridine d$_5$):

| FREQUENCY | PPM | INTENSITY |
|---|---|---|
| 3085.997 | 8.5690 | 93.151 |
| 2789.295 | 7.7452 | 2.522 |
| 2788.014 | 7.7416 | 2.461 |
| 2781.668 | 7.7240 | 2.672 |
| 2670.153 | 7.4143 | 52.389 |
| 2662.006 | 7.3917 | 1.022 |
| 2637.937 | 7.3249 | .817 |
| 2619.105 | 7.2726 | 1.227 |
| 2608.923 | 7.2443 | 2.896 |
| 2607.821 | 7.2413 | 2.914 |
| 2600.569 | 7.2211 | 3.137 |
| 2597.281 | 7.2120 | 1.996 |
| 2589.809 | 7.1912 | 3.315 |
| 2581.491 | 7.1681 | 2.266 |
| 2577.499 | 7.1571 | 1.312 |
| 2573.116 | 7.1449 | 1.565 |
| 2538.173 | 7.0479 | 85.526 |
| 2530.928 | 7.0278 | 2.429 |
| 2523.065 | 7.0059 | 2.336 |
| 2521.838 | 7.0025 | 2.312 |
| 2515.673 | 6.9854 | 1.385 |
| 2514.297 | 6.9816 | 1.249 |
| 1894.281 | 5.2599 | 1.731 |
| 1889.986 | 5.2480 | 1.935 |
| 1883.930 | 5.2312 | 1.955 |
| 1879.631 | 5.2193 | 1.823 |
| 1778.344 | 4.9380 | 1.034 |
| 1721.287 | 4.7796 | 2.783 |
| 1573.832 | 4.3701 | 3.207 |
| 1561.153 | 4.3349 | 3.094 |
| 1391.698 | 3.8644 | 1.793 |
| 1387.597 | 3.8530 | 1.978 |
| 1380.523 | 3.8334 | 1.809 |
| 1376.417 | 3.8220 | 1.527 |
| 1349.161 | 3.7463 | 1.445 |
| 1342.688 | 3.7283 | 3.030 |
| 1335.992 | 3.7097 | 3.109 |
| 1329.527 | 3.6918 | 1.480 |
| 1245.053 | 3.4572 | 1.119 |
| 1233.053 | 3.4239 | 1.055 |
| 1109.056 | 3.0796 | 4.227 |
| 1104.734 | 3.0676 | 21.581 |
| 1083.720 | 3.0092 | 1.329 |
| 1077.008 | 2.9906 | 1.526 |
| 1031.596 | 2.0645 | 3.039 |
| 1024.781 | 2.0456 | 4.820 |
| 1017.982 | 2.8267 | 2.464 |
| 933.976 | 2.5934 | 1.604 |
| 837.857 | 2.3265 | 1.306 |

-continued

| FREQUENCY | PPM | INTENSITY |
|---|---|---|
| 835.753 | 2.3207 | 1.763 |
| 833.609 | 2.3147 | 2.246 |
| 831.269 | 2.3082 | 1.735 |
| 709.321 | 1.9696 | 1.093 |
| 692.847 | 1.9239 | 2.684 |
| 677.031 | 1.8799 | 14.762 |

IR(KBr, $\nu_{max}$ cm$^{-1}$): 3450, 3290, 2930, 1720, 1640, 1560, 1515, 1475, 1455, 1330, ±065.
UV(MeOH, $\nu_{max}$ nm): 367, 218.

EXAMPLE 10

7-[2-(3,4-Dichlorophenyldithio)ethylamino]-9a-methoxymitosane (61).—Method A applied to 3,4-dichlorothiophenol $^1$H NMR data (pyridine) d$_5$):

| FREQUENCY | PPM | INTENSITY |
|---|---|---|
| 3084.858 | 8.5659 | 22.651 |
| 2737.563 | 7.6015 | 6.955 |
| 2669.762 | 7.4133 | 14.063 |
| 2640.258 | 7.3313 | 2.508 |
| 2631.654 | 7.3074 | 11.844 |
| 2621.027 | 7.2779 | 1.371 |
| 2552.501 | 7.0877 | 3.109 |
| 2546.297 | 7.0704 | 5.072 |
| 2537.654 | 7.0464 | 22.116 |
| 1894.292 | 5.2600 | 2.536 |
| 1890.094 | 5.2483 | 2.506 |
| 1883.970 | 5.2313 | 2.855 |
| 1879.783 | 5.2197 | 2.430 |
| 1772.587 | 4.9220 | 1.414 |
| 1576.225 | 4.3768 | 4.099 |
| 1563.539 | 4.3416 | 4.212 |
| 1393.191 | 3.8685 | 2.774 |
| 1389.009 | 3.8569 | 2.818 |
| 1381.991 | 3.8374 | 2.714 |
| 1377.894 | 3.8261 | 2.274 |
| 1349.938 | 3.7484 | 2.676 |
| 1343.449 | 3.7304 | 5.650 |
| 1336.929 | 3.7123 | 5.651 |
| 1330.508 | 3.6945 | 2.513 |
| 1246.457 | 3.4611 | 2.136 |
| 1234.069 | 3.4267 | 1.933 |
| 1106.375 | 3.0721 | 27.896 |
| 1073.644 | 2.9812 | 3.091 |
| 1044.916 | 2.9015 | 4.799 |
| 1038.298 | 2.8831 | 7.779 |
| 1031.673 | 2.8647 | 3.943 |
| 933.135 | 2.5911 | 3.175 |
| 919.103 | 2.5521 | 1.877 |
| 712.794 | 1.9792 | 1.524 |
| 708.146 | 1.9663 | 1.502 |
| 676.000 | 1.8771 | 23.605 |

EXAMPLE 11

7-[2-(3-Trifluoromethylphenyldithio)ethylamino]-9a-methoxymitosane (51).—Method A applied to 3-trifluoromethylthiophenol $^1$H NMR data (pyridine) d$_5$):

| FREQUENCY | PPM | INTENSITY |
|---|---|---|
| 3096.041 | 8.5969 | 3.979 |
| 3086.601 | 8.5707 | 191.394 |
| 2816.428 | 7.8205 | 4.046 |
| 2766.458 | 7.6817 | 2.614 |
| 2759.037 | 7.6111 | 2.944 |
| 2680.739 | 7.4437 | 2.354 |
| 2670.277 | 7.4147 | 94.728 |
| 2653.288 | 7.3675 | 4.565 |

-continued

| FREQUENCY | PPM | INTENSITY |
|---|---|---|
| 2646.995 | 7.3500 | 3.364 |
| 2639.249 | 7.3285 | 3.513 |
| 2549.619 | 7.0796 | 4.014 |
| 2538.277 | 7.0481 | 168.333 |
| 1890.555 | 5.2496 | 2.054 |
| 1884.287 | 5.2322 | 2.269 |
| 1880.154 | 5.2207 | 2.244 |
| 1730.088 | 4.8040 | 36.462 |
| 1573.873 | 4.3702 | 3.649 |
| 1561.173 | 4.3350 | 3.993 |
| 1391.847 | 3.8648 | 2.133 |
| 1387.644 | 3.8531 | 2.307 |
| 1380.627 | 3.8336 | 2.205 |
| 1342.397 | 3.7275 | 3.887 |
| 1335.818 | 3.7092 | 4.271 |
| 1109.074 | 3.0796 | 2.622 |
| 1104.563 | 3.0671 | 31.755 |
| 1046.186 | 2.9050 | 3.531 |
| 1039.326 | 2.8859 | 6.432 |
| 1032.615 | 2.8673 | 3.667 |
| 932.644 | 2.5897 | 2.040 |
| 671.477 | 1.8645 | 21.716 |

EXAMPLE 12

7-[2-(3-Methoxyphenyldithio)ethylamino]-9a-methoxymitosane (54).—Method A applied to 3-methoxythiophenol $^1$H NMR data (pyridine d$_5$):

| FREQUENCY | PPM | INTENSITY |
|---|---|---|
| 3086.415 | 8.5702 | 562.724 |
| 2670.763 | 7.4160 | 276.099 |
| 2590.589 | 7.1934 | 24.212 |
| 2588.595 | 7.1879 | 34.760 |
| 2586.537 | 7.1822 | 24.674 |
| 2584.829 | 7.1774 | 15.856 |
| 2576.794 | 7.1551 | 33.209 |
| 2563.954 | 7.1333 | 30.001 |
| 2561.309 | 7.1121 | 34.129 |
| 2560.105 | 7.1088 | 23.550 |
| 2553.236 | 7.0897 | 20.367 |
| 2533.633 | 7.0491 | 496.430 |
| 2526.218 | 7.0147 | 8.194 |
| 2425.701 | 6.7356 | 15.379 |
| 2422.569 | 6.7269 | 14.307 |
| 2417.424 | 6.7126 | 12.749 |
| 2415.676 | 6.7077 | 13.045 |
| 1892.375 | 5.2560 | 14.143 |
| 1888.677 | 5.2444 | 14.228 |
| 1882.529 | 5.2273 | 17.285 |
| 1873.267 | 5.2155 | 15.537 |
| 1772.130 | 4.9208 | 5.709 |
| 1719.455 | 4.7745 | 11.035 |
| 1576.419 | 4.3773 | 26.798 |
| 1563.627 | 4.3418 | 28.124 |
| 1391.474 | 3.8638 | 13.769 |
| 1337.333 | 3.8523 | 14.672 |
| 1380.333 | 3.8328 | 15.288 |
| 1376.094 | 3.3211 | 12.470 |
| 1352.786 | 3.7563 | 9.557 |
| 1345.640 | 3.7365 | 22.501 |
| 1338.800 | 3.7175 | 23.308 |
| 1332.158 | 3.6991 | 9.726 |
| 1281.868 | 3.5594 | 236.211 |
| 1246.777 | 3.4620 | 9.717 |
| 1234.477 | 3.4278 | 8.759 |
| 1106.624 | 3.0728 | 235.081 |
| 1074.832 | 2.9845 | 13.422 |
| 1070.883 | 2.9736 | 13.378 |
| 1040.474 | 2.8891 | 26.338 |
| 1033.789 | 2.8706 | 50.460 |
| 1026.992 | 2.8517 | 22.622 |
| 932.644 | 2.5897 | 14.174 |
| 920.731 | 2.5566 | 8.501 |
| 693.444 | 1.9255 | 8.385 |

| FREQUENCY | PPM | INTENSITY |
|---|---|---|
| 677.749 | 1.8819 | 156.816 |
| 664.377 | 1.8448 | 18.786 |
| 461.026 | 1.2802 | 32.173 |

IR(KBr, $\nu_{max}$ cm$^{-1}$): 3450, 3300, 2930, 1720, 1638, 1560, 1515, 1478, 1450, 1330, 1065.

UV(MeOH, $\nu_{max}$, nm): 368, 216.

EXAMPLE 13

7-[2-(2-Methoxyphenyldithio)ethylamino]-9a-methoxymitosane (56).—Method A applied to 2-methoxythiophenol $^1$H NMR data (pyridine d$_5$):

| FREQUENCY | PPM | INTENSITY |
|---|---|---|
| 3086.515 | 8.5705 | 103.547 |
| 2778.944 | 7.7164 | 4.168 |
| 2771.012 | 7.6944 | 4.081 |
| 2670.705 | 7.4159 | 51.850 |
| 2568.761 | 7.1328 | 2.967 |
| 2561.119 | 7.1116 | 4.469 |
| 2553.130 | 7.0894 | 4.282 |
| 2538.673 | 7.0493 | 98.737 |
| 2501.730 | 6.9467 | 3.067 |
| 2494.323 | 6.9261 | 4.503 |
| 2486.601 | 6.9047 | 1.993 |
| 2434.187 | 6.7591 | 4.865 |
| 2426.072 | 6.7366 | 4.291 |
| 1892.531 | 5.2551 | 2.952 |
| 1888.248 | 5.2432 | 2.979 |
| 1882.191 | 5.2264 | 3.350 |
| 1877.909 | 5.2145 | 3.233 |
| 1769.650 | 4.9139 | 2.076 |
| 1577.497 | 4.3803 | 4.401 |
| 1564.771 | 4.3450 | 4.774 |
| 1390.507 | 3.8611 | 2.872 |
| 1386.070 | 3.8488 | 3.249 |
| 1379.349 | 3.8301 | 3.096 |
| 1375.131 | 3.8184 | 2.805 |
| 1370.459 | 3.8054 | 1.769 |
| 1363.138 | 3.7851 | 3.147 |
| 1356.287 | 3.7661 | 5.382 |
| 1349.565 | 3.7474 | 5.172 |
| 1342.957 | 3.7291 | 2.223 |
| 1289.212 | 3.5798 | 33.137 |
| 1247.557 | 3.4642 | 3.063 |
| 1235.150 | 3.4297 | 2.866 |
| 1104.941 | 3.0681 | 37.499 |
| 1074.634 | 2.9840 | 4.035 |
| 1070.446 | 2.9724 | 4.152 |
| 1034.998 | 2.8739 | 4.481 |
| 1028.277 | 2.8553 | 7.873 |
| 1021.667 | 2.8369 | 4.503 |
| 933.058 | 2.5909 | 3.839 |
| 715.577 | 1.9870 | 6.097 |
| 682.593 | 1.8954 | 24.161 |

IR(KBr, $\nu_{max}$, cm$^{-1}$): 3450, 3300, 2930, 1720, 1635, 1560, 1515, 1450, 1330, 1065.

UV(MeOH, $\nu_{max}$, nm): 209, 214, 367.

EXAMPLE 14

7-[2-(2-Aminophenyldithio)ethylamino]-9a-methoxymitosane (62).—Method A applied to 2-aminothiophenol $^1$H NMR data (pyridine d$_5$):

| FREQUENCY | PPM | INTENSITY |
|---|---|---|
| 3086.382 | 8.5701 | 86.732 |
| 2671.205 | 7.4173 | 62.983 |
| 2578.881 | 7.1609 | 3.300 |
| 2572.379 | 7.1428 | 5.663 |
| 2566.135 | 7.1255 | 3.459 |
| 2538.819 | 7.0497 | 80.609 |
| 1981.127 | 5.5011 | 3.555 |
| 1891.642 | 5.2526 | 3.601 |
| 1887.582 | 5.2413 | 3.804 |
| 1881.369 | 5.2241 | 4.295 |
| 1877.286 | 5.2128 | 4.002 |
| 1787.037 | 4.9622 | 2.215 |
| 1776.461 | 4.9328 | 3.216 |
| 1765.421 | 4.9021 | 2.113 |
| 1726.603 | 4.7943 | 5.706 |
| 1580.362 | 4.3883 | 6.641 |
| 1567.711 | 4.3531 | 7.123 |
| 1396.170 | 3.8768 | 4.761 |
| 1391.953 | 3.8651 | 5.348 |
| 1385.027 | 3.8459 | 5.751 |
| 1380.690 | 3.8338 | 5.437 |
| 1377.505 | 3.8250 | 5.033 |
| 1370.775 | 3.8063 | 8.789 |
| 1364.034 | 3.7876 | 8.329 |
| 1357.381 | 3.7691 | 3.488 |
| 1244.058 | 3.4544 | 55.742 |
| 1230.981 | 3.4181 | 3.383 |
| 1104.203 | 3.0661 | 59.468 |
| 1095.831 | 3.0428 | 2.087 |
| 1074.561 | 2.9838 | 3.647 |
| 1030.274 | 2.8608 | 7.363 |
| 1023.508 | 2.8420 | 11.992 |
| 1016.755 | 2.8233 | 6.322 |
| 931.694 | 2.5871 | 4.183 |
| 715.588 | 1.9870 | 34.595 |

EXAMPLE 15

7-[2-(4-Aminophenyldithio)ethylamino]-9a-methoxymitosane (43).—Method A applied to 4-aminothiophenol $^1$H NMR data (pyridine d$_5$):

| FREQUENCY | PPM | INTENSITY |
|---|---|---|
| 3097.058 | 8.5997 | 2.074 |
| 3086.103 | 8.5693 | 63.446 |
| 2682.029 | 7.4473 | 1.928 |
| 2670.785 | 7.4161 | 42.263 |
| 2654.773 | 7.3716 | 4.957 |
| 2646.488 | 7.3486 | 4.979 |
| 2549.849 | 7.0803 | 2.125 |
| 2538.595 | 7.0490 | 61.793 |
| 2510.432 | 6.9708 | 1.330 |
| 2423.093 | 6.7283 | 4.293 |
| 2414.889 | 6.7055 | 4.133 |
| 2093.654 | 5.8135 | 4.159 |
| 1902.189 | 5.2819 | 1.410 |
| 1897.989 | 5.2702 | 1.533 |
| 1891.815 | 5.2531 | 1.801 |
| 1887.650 | 5.2415 | 1.791 |
| 1788.714 | 4.9668 | 1.228 |
| 1722.452 | 4.7828 | 1.920 |
| 1711.799 | 4.7532 | 51.957 |
| 1581.821 | 4.3923 | 2.586 |
| 1569.146 | 4.3571 | 2.853 |
| 1390.464 | 3.8609 | 1.603 |
| 1386.294 | 3.8494 | 1.812 |
| 1379.299 | 3.8299 | 1.838 |
| 1375.107 | 3.8183 | 1.764 |
| 1371.339 | 3.8078 | 1.179 |
| 1364.417 | 3.7886 | 2.620 |
| 1358.048 | 3.7709 | 2.919 |
| 1351.641 | 3.7531 | 1.432 |
| 1241.435 | 3.4471 | 1.181 |
| 1228.989 | 3.4126 | 1.076 |
| 1105.040 | 3.0684 | 1.718 |
| 1100.481 | 3.0557 | 19.033 |
| 1091.834 | 3.0317 | 1.020 |

| FREQUENCY | PPM | INTENSITY |
|---|---|---|
| 1086.003 | 3.0155 | 1.050 |
| 1078.584 | 2.9949 | 1.268 |
| 1056.956 | 2.9349 | 1.282 |
| 1050.624 | 2.9173 | 2.037 |
| 1046.337 | 2.9054 | 1.754 |
| 1039.661 | 2.8869 | 2.359 |
| 1032.701 | 2.8675 | 1.549 |
| 930.333 | 2.5833 | 1.355 |
| 723.295 | 2.0084 | 1.102 |
| 698.719 | 1.9402 | 14.859 |
| 689.544 | 1.9147 | 2.050 |
| 558.101 | 1.5497 | 1.018 |
| 461.045 | 1.2802 | 1.183 |
| −56.758 | −.1576 | 35.127 |

IR(KBr, $\nu_{max}$ cm$^{-1}$): 3440, 3360, 3290, 2940, 1720, 1635, 1600, 1510, 1300, 1330.

UV(MeOH, $\lambda_{max}$ nm): 218, 369.

EXAMPLE 16

7-[2-(3-Aminophenyldithio)ethylamino]-9a-methoxymitosane (53).—Method A applied to 3-aminothiophenol $^1$H NMR data (pyridine d$_5$):

| FREQUENCY | PPM | INTENSITY |
|---|---|---|
| 3086.871 | 8.5715 | 374.990 |
| 2691.699 | 7.4742 | 2.504 |
| 2682.064 | 7.4474 | 6.153 |
| 2670.593 | 7.4156 | 273.131 |
| 2588.581 | 7.1878 | 2.271 |
| 2571.392 | 7.1401 | 4.098 |
| 2569.555 | 7.1350 | 6.159 |
| 2559.811 | 7.1080 | 2.805 |
| 2549.477 | 7.0793 | 7.506 |
| 2538.555 | 7.0489 | 343.206 |
| 2527.557 | 7.0184 | 10.512 |
| 2463.709 | 6.8411 | 3.109 |
| 2456.158 | 6.8201 | 4.694 |
| 2408.230 | 6.6870 | 2.705 |
| 2400.366 | 6.6652 | 2.454 |
| 2398.758 | 6.6607 | 2.471 |
| 2044.665 | 5.6775 | 3.737 |
| 1895.598 | 5.2636 | 1.760 |
| 1891.482 | 5.2522 | 1.874 |
| 1885.412 | 5.2353 | 2.269 |
| 1881.100 | 5.2233 | 2.074 |
| 1730.133 | 4.8041 | 64.790 |
| 1579.573 | 4.3861 | 3.851 |
| 1566.945 | 4.3510 | 4.131 |
| 1392.672 | 3.8671 | 2.423 |
| 1388.477 | 3.8555 | 2.439 |
| 1381.578 | 3.8363 | 2.411 |
| 1377.292 | 3.8244 | 2.138 |
| 1347.946 | 3.7429 | 1.646 |
| 1340.937 | 3.7234 | 3.908 |
| 1334.439 | 3.7054 | 4.130 |
| 1327.335 | 3.6857 | 1.781 |
| 1103.126 | 3.0631 | 32.573 |
| 1072.236 | 2.9773 | 1.692 |
| 1016.905 | 2.8237 | 4.041 |
| 1010.123 | 2.8049 | 7.329 |
| 1003.221 | 2.7857 | 3.777 |
| 929.798 | 2.5818 | 1.966 |
| 714.778 | 1.9848 | 1.619 |
| 685.856 | 1.9044 | 16.898 |

EXAMPLE 17

7-[2-(4-Hydroxyphenyldithio)ethylamino]-9a-methoxymitosane (42).—Method A applied to 4-hydroxythiophenol $^1$H NMR data (pyridine d$_5$):

| FREQUENCY | PPM | INTEGRAL | INTENSITY |
|---|---|---|---|
| 3136.440 | 8.7090 | 6.424 | 68.701 |
| 2747.803 | 7.6299 | 1.242 | 15.154 |
| 2739.247 | 7.6061 | 1.336 | 17.730 |
| 2731.869 | 7.5856 | .348 | 3.823 |
| 2721.298 | 7.5563 | 5.725 | 46.476 |
| 2598.368 | 7.2149 | .269 | 2.515 |
| 2589.146 | 7.1893 | 7.546 | 69.914 |
| 2573.746 | 7.1466 | .152 | 5.763 |
| 2570.616 | 7.1379 | 1.138 | 17.960 |
| 2562.036 | 7.1140 | 1.301 | 16.493 |
| 1949.364 | 5.4128 | .230 | 4.049 |
| 1945.208 | 5.4013 | .291 | 4.599 |
| 1938.860 | 5.3837 | .304 | 5.403 |
| 1934.844 | 5.3725 | .367 | 5.444 |
| 1821.705 | 5.0584 | 1.429 | 3.916 |
| 1810.519 | 5.0273 | .516 | 3.981 |
| 1776.864 | 4.9338 | 10.877 | 17.811 |
| 1637.246 | 4.5462 | .514 | 7.855 |
| 1624.515 | 4.5108 | .679 | 8.597 |
| 1442.851 | 4.0064 | .315 | 4.339 |
| 1438.819 | 3.9952 | .305 | 5.098 |
| 1431.777 | 3.9756 | .289 | 5.109 |
| 1427.713 | 3.9644 | .266 | 5.219 |
| 1423.796 | 3.9535 | .310 | 4.558 |
| 1417.071 | 3.9348 | .781 | 10.371 |
| 1410.591 | 3.9168 | .886 | 10.894 |
| 1404.165 | 3.8990 | .429 | 4.641 |
| 1294.248 | 3.5938 | 2.282 | 32.775 |
| 1285.005 | 3.5681 | .744 | 5.315 |
| 1154.198 | 3.2049 | 3.627 | 58.965 |
| 1129.182 | 3.1354 | .453 | 5.115 |
| 1125.913 | 3.1263 | .766 | 5.942 |
| 1103.171 | 3.0632 | .560 | 6.411 |
| 1096.485 | 3.0446 | .924 | 11.653 |
| 1089.858 | 3.0262 | .625 | 6.432 |
| 982.320 | 2.7276 | 1.199 | 5.800 |
| 765.778 | 2.1263 | .369 | 3.738 |
| 748.336 | 2.0779 | 3.529 | 45.305 |

EXAMPLE 18

7-[2-(1-Phenylethylidithio)ethylamino]-9a-methoxymitosane (48).—Method A applied to 1-phenylethane thiol $^1$H NMR data (partial, pyridine d$_5$):

| FREQUENCY | PPM | INTEGRAL | INTENSITY |
|---|---|---|---|
| 1952.473 | 5.4215 | .091 | 5.104 |
| 1948.316 | 5.4100 | .090 | 5.513 |
| 1942.104 | 5.3927 | .112 | 6.418 |
| 1938.031 | 5.3814 | .090 | 6.033 |
| 1848.588 | 5.1331 | .076 | 2.441 |
| 1837.836 | 5.1032 | .148 | 4.239 |
| 1827.564 | 5.0747 | .057 | 1.881 |
| 1775.213 | 4.9293 | .639 | 20.616 |
| 1639.982 | 4.5538 | .198 | 12.917 |
| 1627.323 | 4.5187 | .205 | 14.196 |
| 1521.186 | 4.2239 | .011 | 1.913 |
| 1519.505 | 4.2193 | .025 | 1.950 |
| 1514.020 | 4.2040 | .075 | 6.785 |
| 1512.644 | 4.2002 | .072 | 6.606 |
| 1507.161 | 4.1850 | .089 | 7.200 |
| 1505.450 | 4.1803 | .056 | 6.945 |
| 1500.096 | 4.1654 | .019 | 1.856 |
| 1498.683 | 4.1615 | .015 | 1.741 |
| 1450.041 | 4.0264 | .102 | 7.268 |
| 1445.788 | 4.0146 | .109 | 7.975 |
| 1438.875 | 3.9954 | .116 | 7.796 |
| 1434.671 | 3.9837 | .078 | 6.415 |
| 1377.618 | 3.8253 | .123 | 5.278 |
| 1370.918 | 3.8067 | .352 | 14.614 |
| 1364.196 | 3.7880 | .325 | 14.774 |
| 1357.461 | 3.7693 | .096 | 5.120 |
| 1302.525 | 3.6168 | .185 | 4.369 |
| 1290.379 | 3.5831 | .141 | 3.787 |
| 1177.451 | 3.2695 | .023 | 2.008 |

-continued

| FREQUENCY | PPM | INTEGRAL | INTENSITY |
|---|---|---|---|
| 1169.846 | 3.2484 | .046 | 1.616 |
| 1158.939 | 3.2181 | 1.461 | 127.782 |
| 1139.148 | 3.1631 | .080 | 2.974 |
| 1135.997 | 3.1544 | .072 | 3.988 |
| 1132.619 | 3.1450 | .089 | 3.991 |
| 1128.305 | 3.1330 | .083 | 3.545 |
| 995.594 | 2.7645 | .081 | 3.409 |
| 990.478 | 2.7503 | .319 | 4.937 |
| 965.625 | 2.6813 | .247 | 9.342 |
| 958.849 | 2.6625 | .447 | 17.679 |
| 952.251 | 2.6442 | .191 | 8.417 |
| 771.751 | 2.1430 | .117 | 3.407 |
| 765.016 | 2.1243 | .241 | 6.467 |
| 755.207 | 2.0970 | 1.509 | 59.872 |
| 596.118 | 1.6553 | .398 | 31.993 |
| 594.078 | 1.6496 | .324 | 31.181 |
| 588.980 | 1.6354 | .301 | 33.173 |
| 586.888 | 1.6296 | .366 | 31.940 |

IR(KBr, $\nu_{max}$, cm$^{-1}$): 3430, 3300, 2920, 1720, 1640, 1560, 1510, 1450, 1330, 1220, 1060.
UV(MeOH, $\lambda_{max}$, nm): 369, 220.

EXAMPLE 19

7-[2-(4-Pyridylmethyldithio)ethylamino]-9a-methoxymitosane (64).—Method A applied to 4-pyridylmethane thiol $^1$H NMR data (pyridine d$_5$):

| FREQUENCY | PPM | INTENSITY |
|---|---|---|
| 3174.124 | 8.8137 | 1.559 |
| 3086.504 | 8.5704 | 275.681 |
| 2997.042 | 8.3220 | 1.755 |
| 2751.614 | 7.6405 | 1.621 |
| 2670.799 | 7.4161 | 152.517 |
| 2619.866 | 7.2747 | 2.215 |
| 2594.341 | 7.2038 | 13.449 |
| 2588.514 | 7.1877 | 13.887 |
| 2549.316 | 7.0788 | 10.685 |
| 2538.735 | 7.0494 | 237.966 |
| 2491.394 | 6.9180 | 1.671 |
| 2476.552 | 6.8768 | 1.626 |
| 2455.604 | 6.8186 | 1.879 |
| 1997.041 | 5.2676 | 3.896 |
| 1892.600 | 5.2553 | 3.933 |
| 1886.432 | 5.2331 | 4.161 |
| 1882.279 | 5.2266 | 3.382 |
| 1778.252 | 4.9378 | 2.947 |
| 1720.692 | 4.7779 | 50.899 |
| 1650.169 | 4.5821 | 1.779 |
| 1582.212 | 4.3934 | 6.685 |
| 1569.373 | 4.3578 | 7.394 |
| 1508.983 | 4.1901 | 1.569 |
| 1461.935 | 4.0594 | 1.608 |
| 1414.766 | 3.9285 | 1.617 |
| 1394.661 | 3.8726 | 4.329 |
| 1390.442 | 3.8609 | 4.962 |
| 1383.398 | 3.8413 | 4.919 |
| 1379.350 | 3.8301 | 4.376 |
| 1364.298 | 3.7883 | 31.000 |
| 1340.407 | 3.7220 | 3.834 |
| 1333.778 | 3.7036 | 8.347 |
| 1327.039 | 3.6849 | 8.213 |
| 1320.566 | 3.6669 | 4.287 |
| 1292.880 | 3.5900 | 1.763 |
| 1246.523 | 3.4613 | 3.172 |
| 1233.880 | 3.4262 | 2.958 |
| 1179.559 | 3.2753 | 2.321 |
| 1103.699 | 3.0647 | 60.486 |
| 1077.339 | 2.9915 | 3.363 |
| 963.663 | 2.6897 | 6.328 |
| 961.933 | 2.6710 | 11.830 |
| 955.266 | 2.6525 | 6.534 |
| 934.417 | 2.5946 | 3.978 |
| 336.539 | 2.3229 | 4.536 |

-continued

| FREQUENCY | PPM | INTENSITY |
|---|---|---|
| 334.326 | 2.3167 | 5.550 |
| 832.030 | 2.3105 | 4.390 |
| 699.151 | 1.9414 | 29.860 |
| 487.633 | 1.3540 | 1.511 |
| 332.357 | .9229 | 1.611 |

IR(KBr, $\nu_{max}$, cm$^{-1}$): 3440, 3290, 1720, 1640, 1605, 1560, 1515, 1450, 1330, 1065.

EXAMPLE 20

7-[2-(4-Methyl-2-pyridylmethyldithio)ethylamino]-9a-methoxymitosane (63).—Method A applied to 4-methyl-2-pyridylmethane thiol $^1$H NMR data (pyridine d$_5$):

| FREQUENCY | PPM | INTENSITY |
|---|---|---|
| 3086.419 | 8.5702 | 239.187 |
| 3011.849 | 8.3631 | 21.449 |
| 3007.220 | 8.3503 | 22.256 |
| 2671.331 | 7.4176 | 174.780 |
| 2602.023 | 7.2252 | 20.596 |
| 2594.621 | 7.2046 | 23.915 |
| 2572.270 | 7.1425 | 11.140 |
| 2565.754 | 7.1245 | 20.405 |
| 2559.391 | 7.1068 | 11.861 |
| 2539.018 | 7.0502 | 214.105 |
| 2497.280 | 6.9343 | 23.524 |
| 2492.564 | 6.9212 | 22.510 |
| 2489.765 | 6.9135 | 20.583 |
| 2484.914 | 6.9000 | 18.960 |
| 1831.844 | 5.2532 | 14.661 |
| 1887.614 | 5.2414 | 15.562 |
| 1881.465 | 5.2244 | 17.029 |
| 1877.276 | 5.2127 | 16.821 |
| 1776.235 | 4.9322 | 6.874 |
| 1725.906 | 4.7924 | 10.766 |
| 1582.344 | 4.3938 | 30.818 |
| 1569.610 | 4.3584 | 31.970 |
| 1390.446 | 3.8609 | 17.501 |
| 1386.216 | 3.8492 | 18.460 |
| 1379.317 | 3.8300 | 17.756 |
| 1375.091 | 3.8183 | 15.861 |
| 1351.761 | 3.7535 | 14.772 |
| 1345.005 | 3.7347 | 37.838 |
| 1338.331 | 3.7162 | 38.302 |
| 1331.673 | 3.6977 | 14.907 |
| 1245.659 | 3.4589 | 10.523 |
| 1238.513 | 3.4390 | 8.768 |
| 1235.373 | 3.4303 | 8.455 |
| 1102.135 | 3.0604 | 263.849 |
| 1090.832 | 3.0290 | 3.848 |
| 1074.317 | 2.9831 | 12.033 |
| 1030.168 | 2.8605 | 1.861 |
| 979.513 | 2.7199 | 26.621 |
| 972.717 | 2.7010 | 45.298 |
| 966.020 | 2.6824 | 23.341 |
| 951.597 | 2.6423 | 2.822 |
| 932.901 | 2.5904 | 14.404 |
| 831.018 | 2.3075 | 2.380 |
| 814.241 | 2.2609 | 23.991 |
| 807.604 | 2.2425 | 11.000 |
| 790.332 | 2.1946 | 2.335 |
| 768.225 | 2.1332 | 202.142 |
| 750.042 | 2.0827 | 2.241 |
| 738.922 | 2.0518 | 2.803 |
| 693.260 | 1.9250 | 11.444 |

EXAMPLE 21

7-[2-(4-Pyridyldithio)ethylamino]-9a-methoxymitosane (60).—Method A applied to 4-pyridine thiol $^1$H NMR data (pyridine d$_5$):

| FREQUENCY | PPM | INTENSITY |
|---|---|---|
| 3086.649 | 8.5708 | 57.323 |
| 3054.780 | 8.4824 | 1.620 |
| 2671.319 | 7.4176 | 30.934 |
| 2658.667 | 7.3824 | 2.323 |
| 2653.425 | 7.3679 | 2.151 |
| 2619.587 | 7.2739 | .640 |
| 2556.340 | 7.0997 | 2.460 |
| 2539.166 | 7.0506 | 49.665 |
| 1895.995 | 5.2647 | .779 |
| 1891.977 | 5.2535 | .954 |
| 1885.669 | 5.2360 | 1.121 |
| 1881.501 | 5.2245 | .963 |
| 1790.914 | 4.9729 | .698 |
| 1779.668 | 4.9417 | .867 |
| 1769.467 | 4.9134 | .660 |
| 1719.407 | 4.7744 | 30.763 |
| 1575.456 | 4.3746 | 1.488 |
| 1562.781 | 4.3394 | 1.567 |
| 1395.762 | 3.8757 | 1.280 |
| 1391.530 | 3.8639 | 1.478 |
| 1384.665 | 3.8449 | 1.490 |
| 1380.365 | 3.8329 | 1.149 |
| 1342.279 | 3.7272 | 1.455 |
| 1335.741 | 3.7090 | 1.505 |
| 1328.907 | 3.6900 | .652 |
| 1243.405 | 3.4526 | 1.216 |
| 1230.856 | 3.4178 | .692 |
| 1108.243 | 3.0773 | 16.529 |
| 1104.345 | 3.0665 | 3.000 |
| 1080.133 | 2.9993 | .817 |
| 1043.465 | 2.8974 | 1.560 |
| 1036.679 | 2.8786 | 2.550 |
| 1030.071 | 2.8602 | 1.288 |
| 1004.731 | 2.7899 | .568 |
| 934.708 | 2.5954 | .885 |
| 718.942 | 1.9963 | 1.440 |
| 708.953 | 1.9686 | .887 |
| 676.425 | 1.8783 | 6.760 |

IR(KBr, $\nu_{max}$ cm$^{-1}$): 3440, 3290, 2920, 1720, 1635, 1560, 1510, 1465, 1330, 1065.

UV(MeOH, $\nu_{max}$ nm): 219, 240.7, 368.4.

EXAMPLE 22

7-[2-(3-Methyl-2-imidazolylmethyldithio)ethylamino]-9a-methoxymitosane (59).—Method A applied to 3-methyl-2-imidazolylmethane thiol $^1$H NMR data (pyridine d$_5$):

| FREQUENCY | PPM | INTENSITY |
|---|---|---|
| 3086.225 | 8.5697 | 122.148 |
| 2670.664 | 7.4158 | 66.941 |
| 2577.506 | 7.1571 | 2.084 |
| 2570.864 | 7.1386 | 3.985 |
| 2564.225 | 7.1202 | 2.614 |
| 2538.717 | 7.0494 | 111.690 |
| 2475.041 | 6.8726 | 12.583 |
| 2474.081 | 6.8699 | 11.417 |
| 1991.623 | 5.5302 | 7.553 |
| 1894.038 | 5.2593 | 2.7832 |
| 1889.805 | 5.2475 | 2.936 |
| 1883.545 | 5.2301 | 3.292 |
| 1879.381 | 5.2186 | 3.179 |
| 1773.734 | 4.9252 | 1.616 |
| 1728.614 | 4.7999 | 40.343 |
| 1581.458 | 4.3913 | 5.771 |
| 1568.670 | 4.3558 | 6.640 |
| 1475.622 | 4.0974 | 31.332 |
| 1407.786 | 3.9091 | 2.303 |
| 1390.174 | 3.8602 | 3.404 |
| 1386.082 | 3.8488 | 3.896 |
| 1378.969 | 3.8290 | 3.613 |
| 1374.928 | 3.8178 | 3.102 |
| 1336.207 | 3.7103 | 2.949 |
| 1329.594 | 3.6919 | 7.711 |
| 1322.960 | 3.6735 | 7.860 |
| 1316.368 | 3.6552 | 2.843 |
| 1243.997 | 3.4543 | 1.989 |
| 1229.660 | 3.4145 | 5.643 |
| 1220.716 | 3.3896 | 67.094 |
| 1101.470 | 3.0585 | 53.340 |
| 1073.712 | 2.9814 | 2.303 |
| 963.590 | 2.6756 | 5.806 |
| 956.921 | 2.6571 | 10.710 |
| 950.380 | 2.6390 | 5.439 |
| 931.156 | 2.5856 | 2.799 |
| 836.039 | 2.3215 | 1.994 |
| 833.802 | 2.3153 | 2.506 |
| 831.678 | 2.3094 | 1.746 |
| 732.551 | 2.0341 | 2.020 |
| 703.377 | 1.9531 | 28.078 |

IR(KBr, $\nu_{max}$ cm$^{-1}$): 3440, 3290, 2930, 1715, 1635, 1560, 1505, 1456, 1330, 1065.

UV(MeOH, $\lambda_{max}$ nm): 221, 368, 570.

EXAMPLE 23

7-[2-(2-Amino-2-(ethoxycarbonyl)ethyldithio)ethylamino]-9a-methoxymitosane (40).—Method A applied to ethyl cysteinate $^1$H NMR data (pyridine d$_5$, δ): 1.16(t, 3H, J=8 Hz), 2.00(m, 1H), 2.08(s, 3H), 2.72(m, 1H), 3.00(m, 4H), 3.20(s, 3H), 3.56(bd, 1H, J=16 Hz), 3.72-4.12(m, 3H), 4.20(q, 2H, J=8 Hz), 4.52(d, 1H, J=16 Hz), 5.04(t, 1H, J=12 Hz), 5.36(dd, 1H, J=4, 12 Hz).

IR(KBr, $\nu_{max}$ cm$^{-1}$): 3420, 3290, 2920, 1720, 1630, 1555, 1510, 1445, 1320, 1210, 1055.

UV(MeOH, $\lambda_{max}$, nm): 220, 368.

EXAMPLE 24

7-[2-(2-Methoxycarbonyl)ethyldithio)ethylamino]-9a-methoxymitosane (32).—Method A applied to methyl 2-mercaptopropionate $^1$H NMR data (pyridine d$_5$):

| FREQUENCY | PPM | INTENSITY |
|---|---|---|
| 3036.621 | 8.5708 | 52.985 |
| 2685.541 | 7.4571 | .964 |
| 2671.420 | 7.4178 | 22.011 |
| 2566.711 | 7.1271 | 1.704 |
| 2560.323 | 7.1094 | 3.709 |
| 2553.894 | 7.0915 | 2.468 |
| 2539.174 | 7.0506 | 48.244 |
| 1892.097 | 5.2539 | 2.437 |
| 1887.915 | 5.2423 | 2.408 |
| 1881.776 | 5.2252 | 3.020 |
| 1877.563 | 5.2135 | 2.742 |
| 1789.180 | 4.9681 | 1.329 |
| 1778.437 | 4.9383 | 2.280 |
| 1767.395 | 4.9076 | 1.251 |
| 1714.709 | 4.7613 | 7.032 |
| 1580.911 | 4.3898 | 5.108 |
| 1568.144 | 4.3543 | 5.436 |
| 1545.206 | 4.2906 | 7.521 |
| 1538.974 | 4.2733 | 15.936 |
| 1532.490 | 4.2553 | 9.098 |
| 1393.162 | 3.8685 | 3.150 |
| 1388.980 | 3.8568 | 3.181 |
| 1381.922 | 3.3372 | 3.460 |
| 1377.845 | 3.8259 | 2.862 |
| 1368.102 | 3.7989 | 2.724 |
| 1361.449 | 3.7804 | 6.926 |
| 1354.697 | 3.7616 | 7.225 |
| 1347.991 | 3.7430 | 2.958 |
| 1244.836 | 3.4566 | 5.653 |
| 1232.775 | 3.4231 | 2.030 |
| 1104.313 | 3.0664 | 44.326 |

| FREQUENCY | PPM | INTENSITY |
|---|---|---|
| 1073.331 | 2.9943 | 2.082 |
| 1038.407 | 2.8834 | 9.428 |
| 1031.986 | 2.3656 | 15.920 |
| 1025.699 | 2.8481 | 14.126 |
| 1018.715 | 2.8287 | 10.679 |
| 1011.898 | 1.8098 | 5.869 |
| 934.910 | 2.5960 | 2.371 |
| 713.368 | 1.9808 | 25.764 |
| 667.709 | 1.8541 | 65.234 |

IR(KBr, $\nu_{max}$ cm$^{-1}$): 3340, 3280, 2960, 1740, 1640, 1560, 1520, 1455, 1335, 1230, 1070.
UV(MeOH, $\lambda_{max}$, nm): 368, 220.

EXAMPLE 25

7-[2-Dimethylaminoethyldithio)ethylamino]-9a-methoxymitosane (33).—Method A applied to 2-dimethylaminoethanethiol $^1$H NMR data (pyridine d$_5\delta$): 1.98(s, 9H), 2.00 (bs, 1H), 2.42(m, 2H), 2.58(bs, 1H), 2.75(m, 4H), 2.99(bs, 1H), 3.06(s, 3H), 3.45(bs, 1H), 3.85(m, 3H), 4.39(dd, 1H, J=4, 10 Hz), 4.70(m, 1H), 5.23(dd, 1H, J=4, 10 Hz), 7.16(t, 1H).

EXAMPLE 26

7-[2-(2-Carboxyphenyldithio)ethylamino]-9a-methoxymitosane (34).—Method B applied to 2-mercaptobenzoic acid $^1$H NMR data (pyridine d$_5$):

| FREQUENCY | PPM | INTENSITY |
|---|---|---|
| 3105.777 | 8.6240 | 1.068 |
| 3095.623 | 8.5958 | 1.995 |
| 3086.411 | 8.5702 | 81.437 |
| 3071.395 | 8.5285 | 3.587 |
| 3070.374 | 8.5257 | 3.722 |
| 3063.973 | 8.5079 | 3.207 |
| 3062.956 | 8.5051 | 3.295 |
| 2971.028 | 8.2498 | 3.422 |
| 2962.990 | 8.2275 | 3.681 |
| 2689.885 | 7.4691 | 1.038 |
| 2680.454 | 7.4429 | 1.579 |
| 2670.359 | 7.4149 | 52.522 |
| 2659.752 | 7.3855 | 3.062 |
| 2651.257 | 7.3619 | 3.193 |
| 2644.169 | 7.3422 | 1.826 |
| 2569.382 | 7.1345 | 1.372 |
| 2562.851 | 7.1164 | 4.376 |
| 2555.595 | 7.0962 | 4.721 |
| 2547.992 | 7.0751 | 3.405 |
| 2583.284 | 7.0482 | 72.898 |
| 1895.991 | 5.2647 | 1.861 |
| 1891.918 | 5.2534 | 2.099 |
| 1885.537 | 5.2357 | 2.433 |
| 1881.409 | 5.2242 | 2.263 |
| 1741.321 | 4.8352 | 6.008 |
| 1574.703 | 4.3726 | 3.532 |
| 1561.952 | 4.3371 | 3.914 |
| 1394.094 | 3.8710 | 1.995 |
| 1389.928 | 3.8595 | 2.221 |
| 1383.040 | 3.8404 | 2.121 |
| 1378.894 | 3.8288 | 1.946 |
| 1334.928 | 3.7068 | 2.601 |
| 1328.296 | 3.6883 | 2.745 |
| 1244.108 | 3.4546 | 40.035 |
| 1101.463 | 3.0585 | 29.478 |
| 1066.231 | 2.9607 | 1.652 |
| 1003.478 | 2.7864 | 2.733 |
| 996.779 | 2.7678 | 5.468 |
| 990.106 | 2.7493 | 2.776 |
| 926.202 | 2.5718 | 1.893 |
| 663.304 | 1.8418 | 20.960 |

EXAMPLE 27

7-[2-(4-Nitro-3-carboxyphenyldithio)ethylamino]-9a-methoxymitosane (35).—Method B applied to 5-mercapto-2-nitrobenzoic acid $^1$H NMR data (pyridine d$_5$):

| FREQUENCY | PPM | INTENSITY |
|---|---|---|
| 3036.277 | 8.5698 | 570.775 |
| 2943.307 | 3.1367 | 3.327 |
| 2765.764 | 7.6798 | 5.766 |
| 2757.565 | 7.6571 | 7.210 |
| 2670.599 | 7.4156 | 284.388 |
| 2533.303 | 7.0432 | 503.304 |
| 1888.779 | 5.2447 | 4.822 |
| 1884.614 | 5.2331 | 5.007 |
| 1878.212 | 5.2153 | 5.829 |
| 1874.120 | 5.2040 | 5.266 |
| 1781.017 | 4.9454 | 6.815 |
| 1770.174 | 4.9153 | 10.891 |
| 1759.492 | 4.8857 | 7.774 |
| 1733.376 | 4.8181 | 10.973 |
| 1576.793 | 4.8784 7.352 | |
| 1564.168 | 4.3433 | 7.767 |
| 1391.762 | 3.9646 | 6.383 |
| 1387.619 | 3.8531 | 5.894 |
| 1380.737 | 3.8340 | 6.434 |
| 1376.590 | 3.8114 | 5.132 |
| 1333.456 | 3.8224 | 6.531 |
| 1329.266 | 3.6910 | 6.328 |
| 1244.117 | 3.4546 | 8.549 |
| 1232.499 | 3.4223 | 5.061 |
| 1103.173 | 3.0632 | 77.788 |
| 1062.837 | 2.9512 | 6.516 |
| 1058.740 | 209899 | 6.871 |
| 1013.064 | 2.8130 | 8.054 |
| 1006.409 | 2.7945 | 14.156 |
| 999.788 | 2.7762 | 6.715 |
| 925.557 | 2.5700 | 6.602 |
| 680.086 | 1.8884 | 48.400 |
| 672.145 | 1.8664 | 8.733 |
| 664.121 | 1.8441 | 155.478 |

IR(KBr, $\nu_{max}$, cm$^{-1}$): 3440, 3280, 2930, 1605, 1620, 1640, 1560, 1510, 1455, 1340, 1065.
UV(H$_2$O, $\lambda_{max}$ nm): 220, 368.

EXAMPLE 28

7-[2-(2-Amino-2-carboxyethyldithio)ethylamino]-9a-methoxymitosane (36).—Method B is applied to cysteine.

$^1$H NMR data (D$_2$O):

| FREQUENCY | PPM | INTENSITY |
|---|---|---|
| 1649.415 | 4.5800 | 3.108 |
| 1645.021 | 4.5678 | 3.552 |
| 1638.887 | 4.5508 | 4.085 |
| 1634.273 | 4.5379 | 3.664 |
| 1525.901 | 4.2370 | 2.308 |
| 1515.309 | 4.2076 | 4.240 |
| 1502.937 | 4.1733 | 4.074 |
| 1489.072 | 4.1348 | 3.515 |
| 1462.182 | 4.0601 | 5.478 |
| 1458.281 | 4.0493 | 6.865 |
| 1453.746 | 4.0367 | 11.848 |
| 1447.340 | 4.0189 | 12.514 |
| 1440.997 | 4.0013 | 6.591 |
| 1312.694 | 3.6450 | 5.567 |

-continued

| FREQUENCY | PPM | INTENSITY |
|---|---|---|
| 1308.251 | 3.6327 | 7.686 |
| 1302.226 | 3.6159 | 6.519 |
| 1297.608 | 3.6031 | 5.724 |
| 1196.176 | 3.3215 | 27.550 |
| 1192.345 | 3.3108 | 4.924 |
| 1181.395 | 3.2804 | 6.497 |
| 1177.423 | 3.2694 | 6.949 |
| 1168.542 | 3.2447 | 63.594 |
| 1119.788 | 3.1094 | 6.275 |
| 1111.126 | 3.0853 | 6.867 |
| 1104.602 | 3.0672 | 5.814 |
| 1096.139 | 3.0437 | 9.401 |
| 1089.039 | 3.0240 | 9.495 |
| 1083.236 | 3.0079 | 7.398 |
| 1078.825 | 2.9956 | 10.034 |
| 1072.130 | 2.9770 | 5.638 |
| 1064.763 | 2.9566 | 3.050 |
| 710.980 | 1.9742 | 52.332 |
| −13.126 | −.0364 | 37.147 |

IR(KBr, $\nu_{max}$, cm$^{-1}$): 3440, 3030, 2930, 1720, 1635, 1545, 1495, 1455, 1340, 1065.
UV(H$_2$O, $\lambda_{max}$ nm): 221, 286, 369.

EXAMPLE 29

7-[2-(δ-Glutamylamino)-2-(carboxymethylaminocarbonyl)ethyldithio)ethylamino]-9a-methoxymitosane (37).—Method B is applied to glutathione $^1$H NMR data (D$_2$O):

| FREQUENCY | PPM | INTENSITY |
|---|---|---|
| 1689.759 | 4.6920 | 2.040 |
| 1685.239 | 4.6795 | 1.777 |
| 1643.159 | 4.5626 | 3.892 |
| 1639.038 | 4.5512 | 4.214 |
| 1632.588 | 4.5333 | 4.736 |
| 1628.077 | 4.5207 | 3.302 |
| 1522.085 | 4.2264 | 4.168 |
| 1511.609 | 4.1973 | 3.490 |
| 1500.800 | 4.1673 | 11.262 |
| 1487.527 | 4.1305 | 8.544 |
| 1434.871 | 3.9843 | 6.312 |
| 1429.119 | 3.9683 | 11.942 |
| 1423.005 | 3.9513 | 6.095 |
| 1360.220 | 3.7770 | 2.224 |
| 1342.556 | 3.7279 | 15.731 |
| 1337.863 | 3.7149 | 15.604 |
| 1320.595 | 3.6669 | 2.975 |
| 1307.367 | 3.6302 | 9.377 |
| 1297.536 | 3.6029 | 5.696 |
| 1293.109 | 3.5906 | 8.531 |
| 1248.183 | 3.4659 | 1.820 |
| 1222.128 | 3.3935 | 4.777 |
| 1192.165 | 3.3103 | 1.559 |
| 1165.228 | 3.2355 | 64.295 |
| 1149.618 | 3.1922 | 5.402 |
| 1145.417 | 3.1805 | 5.224 |
| 1083.362 | 3.0082 | 9.800 |
| 1070.734 | 2.9731 | 11.274 |
| 1065.367 | 2.9582 | 11.063 |
| 1060.328 | 2.9443 | 7.567 |
| 1055.097 | 2.9297 | 7.872 |
| 1041.201 | 2.8911 | 4.945 |
| 905.486 | 2.5143 | 6.203 |
| 897.491 | 2.4921 | 10.938 |
| 890.187 | 2.4718 | 7.881 |
| 763.565 | 2.1202 | 8.676 |
| 756.686 | 2.1011 | 8.464 |
| 702.759 | 1.9514 | 46.428 |
| 675.381 | 1.8754 | 3.776 |
| 614.279 | 1.7057 | 7.124 |
| −16.375 | −.0455 | 71.146 |

EXAMPLE 30

7-[2-(2-Amino-2-((1-carboxy-3-methyl-1-butyl)aminocarbonyl)ethyldithio)ethylamino]-9a-methoxymitosane (38).—Method B is applied to L-cysteinyl(-L-)leucine $^1$H NMR data (D$_2$O):

| FREQUENCY | PPM | INTENSITY |
|---|---|---|
| 1651.506 | 4.5858 | 2.924 |
| 1647.060 | 4.5734 | 3.172 |
| 1640.615 | 4.5555 | 3.530 |
| 1635.941 | 4.5426 | 3.165 |
| 1534.085 | 4.2597 | 2.320 |
| 1526.032 | 4.2374 | 3.996 |
| 1515.102 | 4.2070 | 8.668 |
| 1509.929 | 4.1927 | 7.312 |
| 1502.857 | 4.1730 | 7.199 |
| 1488.866 | 4.1342 | 4.838 |
| 1448.667 | 4.0226 | 3.816 |
| 1442.515 | 4.0055 | 7.090 |
| 1436.264 | 3.9881 | 4.773 |
| 1310.487 | 3.6389 | 5.831 |
| 1296.868 | 3.6011 | 5.243 |
| 1227.979 | 3.4098 | 2.982 |
| 1209.376 | 3.3581 | 3.556 |
| 1204.976 | 3.3459 | 3.358 |
| 1197.754 | 3.3258 | 20.161 |
| 1196.599 | 3.3226 | 19.817 |
| 1190.217 | 3.3049 | 4.000 |
| 1178.748 | 3.2731 | 2.371 |
| 1171.258 | 3.2523 | 28.654 |
| 1170.198 | 3.2493 | 25.827 |
| 1147.478 | 3.1862 | 2.328 |
| 1140.928 | 3.1681 | 2,300 |
| 1112.099 | 3.0880 | 3.440 |
| 1104.789 | 3.0677 | 3.880 |
| 1090.655 | 3.0285 | 10.625 |
| 1084.782 | 3.0121 | 7.076 |
| 964.867 | 2.6792 | 2.187 |
| 708.722 | 1.9679 | 21.305 |
| 688.172 | 1.9109 | 2.286 |
| 682.736 | 1.8958 | 2.129 |
| 585.757 | 1.6265 | 4.378 |
| 577.064 | 1.6024 | 9.258 |
| 571.316 | 1.5864 | 10.734 |
| 552.828 | 1.5351 | 2.644 |
| 326.817 | .9075 | 13.468 |
| 321.984 | .8941 | 19.288 |
| 313.339 | .8701 | 14.706 |

EXAMPLE 31

7-[2-(2-Carboxyethyldithio)ethylamino]-9a-methoxymitosane (49).—Method B applied to 2-mercaptopropionic acid $^1$H NMR data (pyridine d$_5$):

| FREQUENCY | PPM | INTENSITY |
|---|---|---|
| 3173.918 | 8.8132 | 1.482 |
| 3107.623 | 8.6291 | 1.70 |
| 3098.097 | 8.6026 | 2.962 |
| 3086.067 | 8.5692 | 245.556 |
| 2996.455 | 8.3204 | 1.700 |
| 2750.459 | 7.6373 | 1.882 |
| 2691.271 | 7.4730 | 2.046 |
| 2682,509 | 7.4487 | 3.099 |
| 2670.109 | 7.4142 | 179.860 |
| 2618.587 | 7.2712 | 1.691 |
| 2597.614 | 7.2129 | 2.079 |
| 2591.598 | 7.1962 | 3.879 |
| 2559.664 | 7.1075 | 1.952 |
| 2550.756 | 7.0828 | 3.249 |
| 2538.040 | 7.0475 | 223.178 |
| 2455.884 | 6.8194 | 1.564 |
| 1879.133 | 5.2179 | 2.486 |

-continued

| FREQUENCY | PPM | INTENSITY |
| --- | --- | --- |
| 1874.974 | 5.2063 | 2.732 |
| 1868.493 | 5.1883 | 3.057 |
| 1864.431 | 5.1771 | 2.916 |
| 1757.132 | 4.8791 | 2.396 |
| 1746.322 | 4.8491 | 4.493 |
| 1724.357 | 4.7881 | 12.748 |
| 1578.370 | 4.3827 | 5.360 |
| 1565.635 | 4.3474 | 5.878 |
| 1383.183 | 3.8408 | 3.558 |
| 1379.027 | 3.8292 | 3.816 |
| 1372.105 | 3.8100 | 5.416 |
| 1365.216 | 3.7909 | 6.123 |
| 1358.754 | 3.7729 | 5.974 |
| 1352.431 | 3.7554 | 2.609 |
| 1244.376 | 3.4553 | 3.440 |
| 1232.982 | 3.4237 | 2.766 |
| 1154.455 | 3.2056 | 3.198 |
| 1150.466 | 3.1946 | 3.935 |
| 1147.759 | 3.1870 | 4.117 |
| 1143.257 | 3.1745 | 8.252 |
| 1136.033 | 3.1545 | 5.235 |
| 1102.572 | 3.0616 | 41.921 |
| 1059.477 | 2.9419 | 3.700 |
| 1030.728 | 2.8621 | 4.972 |
| 1024.210 | 2.8440 | 8.520 |
| 1016.050 | 2.8213 | 6.968 |
| 1008.250 | 2.7997 | 7.948 |
| 1000.938 | 2.7794 | 3.981 |
| 930.084 | 2.5826 | 3.740 |
| 747.720 | 2.0762 | 1.353 |
| 706.055 | 1.9605 | 30.939 |
| 663.989 | 1.8437 | 86.533 |

EXAMPLE 32

7-[2-(4-Nitrophenyldithio)ethylamino]-9a-methoxy-1a-methylmitosane (41)

To a solution of 1a-methyl mitomycin A (98 mg, 0.28 mM (L. Cheng et al., J. Med. Chem. 20, 767 (1977)) in deoxygenated methanol (5 ml) was added at 0 deg. C. and under an argon atmosphere, p-nitrophenyldithioethylamine hydrochloride (81 mg) followed by addition of triethylamine (70 ul). The reaction mixture was allowed to warm up to room temperature and after 3.5 hrs. the reaction was almost complete as evidenced by thin layer chromatography (silica gel, 5% v/v MeOH in $CH_2Cl_2$). The reaction mixture was concentrated under reduced pressure and the resulting residue chromatographed twice on silica gel using 5% v/v MeON in $CH_2Cl_2$ to obtain the title compound pure, as a blue amorphous solid (68 mg, 43%).

$^1$H NMR data (pyridine d$_5$):

| FREQUENCY | PPM | INTENSITY |
| --- | --- | --- |
| 3086.194 | 8.5696 | 7.327 |
| 2909.668 | 8.0794 | 2.697 |
| 2906.985 | 8.0720 | 15.677 |
| 2900.119 | 8.0529 | 6.644 |
| 2898.157 | 8.0474 | 19.406 |
| 2728.645 | 7.5767 | 3.423 |
| 2726.000 | 7.5694 | 19.607 |
| 2724.024 | 7.5639 | 6.419 |
| 2717.205 | 7.5450 | 17.571 |
| 2714.433 | 7.5373 | 2.811 |
| 2670.880 | 7.4163 | 3.934 |
| 2592.925 | 7.1999 | 1.363 |
| 2573.965 | 7.1472 | 2.396 |
| 2567.475 | 7.1292 | 4.678 |
| 2560.978 | 7.1112 | 2.414 |
| 2538.815 | 7.0496 | 7.465 |
| 1989.189 | 5.5235 | 17.248 |
| 1869.362 | 5.1907 | 5.028 |
| 1865.031 | 5.1787 | 5.134 |
| 1859.039 | 5.1621 | 5.865 |
| 1854.684 | 5.1500 | 5.442 |
| 1713.379 | 4.7576 | 27.482 |
| 1676.655 | 4.6556 | 5.491 |
| 1665.804 | 4.6255 | 6.942 |
| 1654.740 | 4.5948 | 4.781 |
| 1546.359 | 4.2938 | 8.676 |
| 1533.366 | 4.2578 | 9.586 |
| 1378.895 | 3.8288 | 4.703 |
| 1374.570 | 3.8168 | 5.175 |
| 1367.615 | 3.7975 | 5.090 |
| 1363.257 | 3.7854 | 4.810 |
| 1360.238 | 3.7770 | 3.127 |
| 1353.560 | 3.7585 | 7.748 |
| 1346.877 | 3.7399 | 8.054 |
| 1340.210 | 3.7214 | 3.084 |
| 1217.740 | 3.3814 | 5.383 |
| 1215.699 | 3.3757 | 5.734 |
| 1204.960 | 3.3459 | 4.905 |
| 1203.034 | 3.3405 | 4.576 |
| 1108.963 | 3.0793 | 2.613 |
| 1096.620 | 3.0450 | 64.271 |
| 1063.680 | 2.9536 | 7.456 |
| 1056.979 | 2.9350 | 14.726 |
| 1050.296 | 2.9164 | 7.013 |
| 858.399 | 2.3836 | 9.631 |
| 853.826 | 2.3709 | 10.974 |
| 758.850 | 2.1071 | 2.474 |
| 753.017 | 2.0909 | 54.711 |
| 738.462 | 2.0505 | 1.558 |
| 723.515 | 2.0090 | 6.130 |
| 721.571 | 2.0036 | 6.123 |
| 719.009 | 1.9965 | 5.626 |
| 717.087 | 1.9912 | 5.387 |
| 675.259 | 1.8750 | 51.667 |
| 531.663 | 1.4763 | 1.417 |
| 37.518 | .1042 | 2.929 |
| −57.316 | −.1592 | 119.809 |
| −59.990 | −.1666 | 6.098 |

IR(KBr, $\nu_{max}$, cm$^{-1}$): 3460, 3300, 2950, 1755, 1640, 1560, 1515, 1455, 1430, 1415, 1330, 1225, 1060.

UV(MeOH, $\lambda_{max}$, nm): 369 and 220.

EXAMPLE 33

7-[2-(3-Nitro-2-pyridyldithio)propylamino]-9a-methoxymitosane (44)

To a solution of 7-dimethylaminomethyleneamino-9a-methoxymitosane (744 mg, 1.91 mM) in deoxygenated methanol (12 ml) at about 0 deg. C. were added sequentially under stirring, 3-(4-nitro-phenyldithio)-propylamine hydrochloride (1.55 g), prepared in the manor described in Ser. No. 581,291 from 3-mercaptopropylamine and employing the deBrois procedure using methoxycarbonylsulfenyl chloride, and triethylamine (774 ul). The reaction mixture was sonicated and allowed to stand at room temperature for 16 hours. Thin layer chromatography (silica gel, 10% MeOH in $CH_2Cl_2$) revealed that a major faster blue component had been formed in addition to the presence of traces of starting material (green) and mitomycin C. The reaction mixture was concentrated under reduced pressure and the resulting residue was chromatrahed twice over silica gel using 5-10% v/v MeOH in $CH_2Cl_2$ to obtain the title compound as the faster blue component, isolated as an amorphous blue solid.

$^1$H NMR data (pyridine d$_5$,)

| FREQUENCY | PPM | INTENSITY |
| --- | --- | --- |
| 3146.622 | 8.7374 | 10.656 |
| 3145.334 | 8.7338 | 12.153 |

| FREQUENCY | PPM | INTENSITY |
|---|---|---|
| 3142.191 | 8.7251 | 12.558 |
| 3140.880 | 8.7214 | 12.868 |
| 3098.074 | 8.6026 | 12.988 |
| 3086.605 | 8.5707 | 368.754 |
| 3007.372 | 8.3507 | 10.609 |
| 2998.735 | 8.3267 | 11.623 |
| 2997.529 | 8.3234 | 13.004 |
| 2751.247 | 7.6395 | 2.991 |
| 2682.257 | 7.4480 | 8.358 |
| 2670.888 | 7.4164 | 158.635 |
| 2619.438 | 7.2735 | 3.486 |
| 2589.946 | 7.1916 | 15.559 |
| 2585.500 | 7.1793 | 13.743 |
| 2581.808 | 7.1690 | 13.827 |
| 2577.322 | 7.1566 | 11.818 |
| 2550.648 | 7.0825 | 13.308 |
| 2538.876 | 7.0498 | 342.655 |
| 2489.224 | 6.9119 | 7.269 |
| 2456.328 | 6.8206 | 2.69 |
| 1879.962 | 5.2202 | 6.152 |
| 1875.717 | 5.2084 | 6.156 |
| 1869.761 | 5.1919 | 7.341 |
| 1865.544 | 5.1801 | 6.872 |
| 1783.865 | 4.9533 | 5.026 |
| 1773.046 | 4.9233 | 8.191 |
| 1762.088 | 4.8929 | 6.240 |
| 1726.635 | 4.7944 | 152.085 |
| 1587.007 | 4.4067 | 13.659 |
| 1574.363 | 4.3716 | 14.231 |
| 1386.003 | 3.8486 | 8.039 |
| 1381.797 | 3.8369 | 8.877 |
| 1374.826 | 3.8175 | 8.285 |
| 1370.733 | 3.8062 | 7.384 |
| 1295.122 | 3.5962 | 6.311 |
| 1290.268 | 3.5828 | 13.374 |
| 1283.643 | 3.5644 | 13.845 |
| 1276.626 | 3.5449 | 6.611 |
| 1247.654 | 3.4644 | 7.155 |
| 1234.232 | 3.4272 | 6.323 |
| 1174.396 | 3.2610 | 2.108 |
| 1114.136 | 3.0937 | 3.007 |
| 1103.806 | 3.0650 | 119.700 |
| 1095.938 | 3.0431 | 4.299 |
| 1078.188 | 2.9939 | 6.641 |
| 1050.017 | 2.9156 | 15.755 |
| 1042.930 | 2.8960 | 30.469 |
| 1036.059 | 2.8769 | 16.193 |
| 934.212 | 2.5941 | 6.742 |
| 713.529 | 1.9813 | 58.234 |
| 685.209 | 1.9027 | 5.453 |
| 678.187 | 1.8832 | 14.115 |
| 671.329 | 1.8641 | 19.760 |
| 664.370 | 1.8448 | 13.086 |
| 657.421 | 1.8255 | 4.108 |
| 402.644 | 1.1180 | 1.812 |
| 242.843 | .6743 | 2.244 |
| 235.548 | .6541 | 1.981 |

EXAMPLE 34

7-[2-(4-Nitrophenyldithio)propylamino]-9a-methoxymitosane (45)

The title compound was prepared according to Method A using Compound No. 33 and 4-nitrothiophenol as reactants.

$^1$H NMR data (pyridine $d_5$):

| FREQUENCY | PPM | INTENSITY |
|---|---|---|
| 3086.648 | 8.5708 | 46.700 |
| 2904.541 | 8.0651 | 3.192 |
| 2895.707 | 8.0406 | 3.355 |
| 2725.964 | 7.5693 | 3.967 |
| 2717.144 | 7.5448 | 3.720 |
| 2670.822 | 7.4162 | 19.799 |
| 2538.767 | 7.0495 | 43.357 |
| 2495.434 | 6.9292 | .924 |

| FREQUENCY | PPM | INTENSITY |
|---|---|---|
| 1879.667 | 5.2193 | .949 |
| 1875.487 | 5.2077 | .880 |
| 1778.272 | 4.9378 | .907 |
| 1725.693 | 4.7918 | 11.856 |
| 1588.217 | 4.4101 | 1.702 |
| 1575.419 | 4.3745 | 1.802 |
| 1391.549 | 3.8640 | .949 |
| 1387.471 | 3.8526 | 1.012 |
| 1380.402 | 3.8330 | .994 |
| 1262.702 | 3.5062 | .936 |
| 1256.047 | 3.4877 | 2.170 |
| 1249.302 | 3.4690 | 2.734 |
| 1242.686 | 3.4506 | 1.129 |
| 1236.092 | 3.4323 | .826 |
| 1104.391 | 3.0666 | 12.996 |
| 986.877 | 2.7403 | 1.868 |
| 979.734 | 2.7205 | 2.943 |
| 972.546 | 2.7005 | 1.812 |
| 937.074 | 2.6020 | .832 |
| 717.038 | 1.9910 | .829 |
| 697.821 | 1.9377 | 7.913 |
| 665.479 | 1.8479 | 1.475 |
| 658.432 | 1.8283 | 1.961 |
| 651.446 | 1.8089 | 1.380 |

The results of antitumor evaluation of the above substances is summarized in the table which follows. The test data involves two experimental animal tumors, P-388 leukemia in mice and B16 melanoma in mice. In addition, the present substances were tested for cytotoxic activity in vitro.

The in vitro cytotoxicity assay involved growing various mammalian tumor cells, including human tumor cells, on microtitre plates employing established tissue culture methods. The concentration of each compound required to inhibit cell growth by 50% ($IC_{50}$) was then determined by a four-fold serial dilution technique. The validity of the method has been supported by a report published in the "Proceedings of the American Association for Cancer Research", Vol. 25, 328, p. 1391 (1984). Tumor cells of one or more of the following types were employed for each compound tested: B16-F10 murine melanoma; C26 murine colon; Moser human colon; M109 murine lung; and RCA human colon. A wide range of $IC_{50}$ values was observed, but quantitative comparisons on the basis of these values were not made. The lowest $IC_{50}$ value, 0.66 mcg/ml, was observed with Compound 26341 against the B16-F10 murine melanoma. In that system mitomycin C exhibits $IC_{50}$ values in the range of 3–30 mcg/ml. Each of the claimed compounds was shown to be active ($IC_{50} < 500$ mcg/ml).

P-388 Murine Leukemia

The test protocol involved $CDF_1$ female mice implanted intraperitoneally with a tumor inoculum of $10^6$ ascites cells of P-388 murine leukemia and treated with various doses of a test compound, or with mitomycin C. The compounds were administered by intraperitoneal injection. Groups of six mice were used for each dosage amount and they were treated with a single dose of the compound on the day of inoculation. A group of ten saline treated control mice was included in each series of experiments. The mitomycin C treated groups were included as a positive control. A 30 day protocol was employed with the mean survival time in days being determined for each group of mice and the number of survivors at the end of the 30 day period being noted. The mice were weighed before treatment and again on day six. The change in weight was taken as a measure of drug toxicity. Mice weighing 20 grams each were employed and a loss in weight of up to approximately 2 grams was not considered excessive. The results were determined in terms of % T/C which is the ratio of the mean survival time of the treated group to the mean survival time of the saline treated control group times 100. The saline treated control animals usually died within nine days. The "maximum effect" in the table is expressed as % T/C and the dose giving that effect is reported. The values in parenthesis are the values obtained with mitomycin C as the positive control in the same experiment. Thus a measure of the relative activity of the present substances to mitomycin C can be estimated. A minimum effect in terms of % T/C was considered to be 125. The minimum effective dose reported in the following table is that dose giving a % T/C of approximately 125. The two values given in each instance in the "average weight change" column are respectively the average weight change per mouse at the maximum effective dose and at the minimum effective dose.

B16 Melanoma

BDF$_1$ mice were employed in the B16 melanoma test. They were inoculated subcutaneously with the tumor implant. A 60 day protocol was used. Groups of ten mice were used for each dosage amount tested and the mean survival time for each group was determined. For each dosage level, the test animals were treated with the test compound on days 1, 5, and 9 by the intravenous route. Control animals which had been inoculated in the same way as test animals and treated with the injection vehicle only containing no drug exhibited a mean survival time of 18.5 to 26 days. The survival time relative to that of the controls (% T/C) was used as a measure of effectiveness. A % T/C value of 140 or greater was considered significant tumor inhibition. The value shown in parenthesis is the % T/C for mitomycin C in the same experiment. Several of the compounds show antitumor effectiveness clearly superior to that of mitomycin C. Examples demonstrating the biggest difference in ratio of activity (% T/C compound/% T/C mitomycin C) are Compound Nos. 43, 56, and 60.

In view of the antitumor activity observed in experimental animal tumors, and the lack of undue toxicity as compared to mitomycin C, the invention includes use of the substances of the present invention for inhibiting mammalian tumors. For this purpose they are administered systematically to a mammal bearing a tumor in substantially non-toxic antitumor effective dose.

The compounds of the present invention are intended primarily for use by injection in much the same way and for some of the same purposes as mitomycin C. Somewhat larger or smaller doses may be employed depending upon the particular tumor sensitivity. They are readily distributed as dry pharmaceutical compositions containing diluents, buffers, stabilizers, solubilizers, and ingredients contributing to pharmaceutical elegance. These compositions are then constituted with an injectable liquid medium extemporaneously just prior to use. Suitable injectable liquids include water, isotonic saline, etc.

Antitumor Activity of Compounds of Formula IX
($Alk_2$ is $-CH_2CH_2-$, and R is H)

| Compound No. (BMY) | Example Number | $R^9$ | B16 Melanoma Optimal Effect (mouse i.v.) | | P-388 Murine Leukemia | | | Average Wt. Change |
|---|---|---|---|---|---|---|---|---|
| | | | | | Maximum Effect | | Minimum Effect | |
| | | | Dose | % T/C* | Dose* | % T/C* | Dose | |
| 32(26341) | 24 | $CH_3CO_2CH_2CH_2-$ | | | 6.4(3.2) | >333(>333) | <0.2 | +0.3, +1.6 |
| 33(26881) | 25 | $(CH_3)_2NCH_2CH_2$ | | | 12.8(4.8) | 167(172) | 6.4 | −1.2, −0.2 |
| 34(26678) | 26 | (o-methyl benzoate, $CO_2Na$) | | | 3.2(4.8) | 150(195) | 0.2 | +0.5, +0.3 |
| 35(26712) | 27 | ($NO_2$, $CO_2Na$ substituted benzene) | 6.4 | 147(124) | 12.8(3.2) | 322(233) | 0.8 | −0.6, +0.8 |
| 36(26711) | 28 | $HO_2CCHCH_2-$ with $NH_2$ | 6.4 | 163(124) | 12.8(3.2) | 306(233) | 0.4 | −1.8, +0.7 |
| 37(26733) | 29 | $NaO_2CCHCH_2CH_2CONH\backslash$ $NH_2$ $CHCH_2-$ / $NaO_2CCH_2NHCO$ | 9.6 | 179(142) | 12.8(4.8) | 144(239) | 6.4 | −0.1, +0.5 |
| 38(26880) | 30 | $HO_2C\backslash$ $NH_2$ / $CHNHCOCHCH_2-$ / $(CH_3)_2CHCH_2$ | | | 6.4(4.8) | 167(172) | 0.8 | +0.7, +1.1 |

-continued
Antitumor Activity of Compounds of Formula IX
(Alk$_2$ is —CH$_2$CH$_2$—, and R is H)

| Compound No. (BMY) | Example Number | R$^9$ | B16 Melanoma Optimal Effect (mouse i.v.) Dose | % T/C* | P-388 Murine Leukemia Maximum Effect Dose* | % T/C* | Minimum Effect Dose | Average Wt. Change |
|---|---|---|---|---|---|---|---|---|
| 39(26187) | 1 | Cl—C$_6$H$_4$— | | | 25.6(4.8) | 233(233) | <0.2 | −1.9, +0.6 |
| 40(26190) | 23 | C$_2$H$_5$O$_2$CCH(NH$_2$)CH$_2$— | | | 25.6(4.8) | 283(233) | <0.2 | −0.9, +1.5 |
| 41(26339) | 32 | NO$_2$—C$_6$H$_4$— (R is methyl) | | | 3.2(3.2) | 167(>333) | 1.6 | +1.2, +1.8 |
| 42(26340) | 17 | HO—C$_6$H$_4$— | 3.2 | 148(112) | 12.8(3.2) | >333(>333) | <0.2 | −1.7, +1.7 |
| 43(26107) | 15 | NH$_2$—C$_6$H$_4$— | 3.2<br>2.4 | 188(112)<br>211(145) | 12.8(4.8) | >333(>333) | <0.2 | −4.5, +1.7 |
| 44(26495) | 33 | 3-NO$_2$-2-pyridyl (Alk$_2$ is —CH$_2$CH$_2$CH$_2$—) | | | 12,8(4.8) | 200(275) | 0.8 | −1.2, +1.2 |
| 45(26496) | 34 | NO$_2$—C$_6$H$_4$— (Alk$_2$ is —CH$_2$CH$_2$CH$_2$—) | | | 25.6(4.8) | 200(275) | 1.6 | 0, +0.3 |
| 46(26646) | 3 | F—C$_6$H$_4$— | 2.4 | 206(153) | 12.8(4.8) | 186(195) | 0.4 | −0.3, +0.7 |
| 47(26650) | 2 | Br—C$_6$H$_4$— | | | 12.8(4.8) | 182(195) | 1.6 | −0.4, +1.3 |
| 48(26112) | 18 | C$_6$H$_5$—CH(CH$_3$)— | | | 3.2(4.8) | 167(>333) | <0.2 | −2.0, +1.2 |
| 49(26679) | 31 | NaO$_2$CCH$_2$CH$_2$— | | | 12.8(4.8) | 191(195) | 0.4 | =0.8, +0.5 |
| 50(26681) | 7 | 2,4-Cl$_2$-C$_6$H$_3$— | | | 6.4(4.8) | 173(195) | 0.4 | −0.4, +0.5 |

-continued
Antitumor Activity of Compounds of Formula IX
(Alk$_2$ is —CH$_2$CH$_2$—, and R is H)
| Compound No. (BMY) | Example Number | R$^9$ | B16 Melanoma Optimal Effect (mouse i.v.) Dose | % T/C* | P-388 Murine Leukemia Maximum Effect Dose* | % T/C* | Minimum Effect Dose | Average Wt. Change |
|---|---|---|---|---|---|---|---|---|
| 51(26682) | 11 | 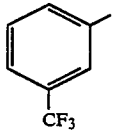 | | | 6.4(4.8) | 182(195) | 0.8 | +0.3, −0.1 |
| 52(26683) | 6 | 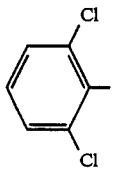 | | | 12.8(4.8) | 168(195) | 1.6 | −0.8, +0.9 |
| 53(26702) | 16 | 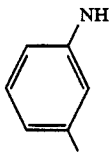 | | | 12.8(4.8) | 105(195) | — | +1.0 — |
| 54(26708) | 12 | 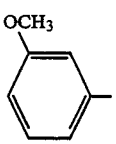 | 1.6 | 216(149) | 12.8(4.8) | 222(233) | 0.8 | −0.3, +0.9 |
| 55(26709) | 4 | 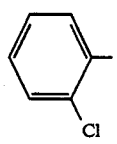 | | | 12.8(4.8) | 183(233) | 0.8 | −0.2, +0.8 |
| 56(26713) | 13 | 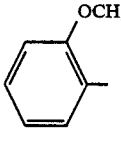 | 1.6 | 251(149) | 12.8(3.2) | 250(233) | 0.4 | −2.9, +0.9 |
| 57(26715) | 9 | 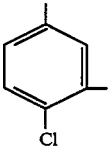 | 4.8 | 209(153) | 12.8(3.2) | 194(233) | 0.2 | −0.7, +1.4 |
| 58(26716) | 8 | 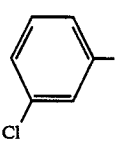 | 6.4 | 209(153) | 12.8(3.2) | 211(233) | 0.1 | −0.2, +1.3 |
| 59(26723) | 22 | 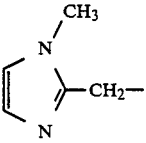 | 4.8<br>4.8 | 226(179)<br>187(142) | 12.8(4.8) | 322(239) | 6.4 | −2.0, −0.8 |

-continued

Antitumor Activity of Compounds of Formula IX
(Alk₂ is —CH₂CH₂—, and R is H)

| Compound No. (BMY) | Example Number | R⁹ | B16 Melanoma Optimal Effect (mouse i.v.) | | P-388 Murine Leukemia Maximum Effect | | Minimum Effect Dose | Average Wt. Change |
|---|---|---|---|---|---|---|---|---|
| | | | Dose | % T/C* | Dose* | % T/C* | | |
| 60(26731) | 21 | 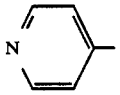 | 9.6 | 251(149) | 12.8(4.8) | 256(239) | 3.2 | −1.9, +0.2 |
| 61 (26732) | 10 | 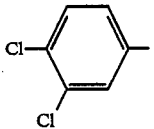 | | | 12.8(4.8) | 150(239) | 3.2 | −1.3, +3.2 |
| 62(26857) | 14 | 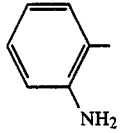 | | | 12.8(4.8) | 139(239) | 12.8 | +0.6, +0.6 |
| 63(26858) | 20 | 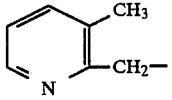 | | | 6.4(4.8) | 144(239) | 1.6 | −1.7, +0.5 |
| 64(26861) | 19 | 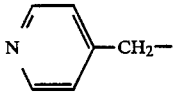 | 3.2 | 173(149) | 6.4(4.8) | 183(239) | 1.6 | −2.1, +0.8 |
| 65(26879) | 5 | 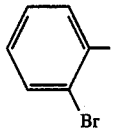 | | | 3.2(4.8) | 178(172) | 0.8 | +0.4, +0.5 |

We claim:
1. A compound selected from the group consisting of Compounds Nos. (32)–(65) identified as follows:
(32) 7-[2-(2-(Methoxycarbonyl)ethyldithio)ethylamino]-9a-methoxymitosane
(33) 7-[2-(2-Dimethylaminoethyldithio)ethylamino]-9a-methoxymitosane
(34) 7-[2-82-Carboxyphenyldithio)ethylamino]-9a-methoxymitosane
(35) 7-[2-(4-Nitro-3-carboxyphenyldithio)ethylamino]-9a-methoxymitosane
(36) 7-[2-(2-Amino-2-carboxyethyldithio)ethylamino]-9a-methoxymitosane
(37) 7-([2-(δ-Glutamylamino)-2-(carboxymethylaminocarbonylethyldithio)ethylamino]-9a-methoxymitosane
(38) 7-[2-Amino-2-((1-carboxy-3-methyl-1-butyl)aminocarbonyl)ethyldithio)ethylamino]-9a-methoxymitosane
(39) 7-[2-(4-Chlorophenyldithio)ethylamino]-9a-methoxymitosane
(40) 7-[2-(2-Amino-2-(ethoxycarbonyl)ethyldithio)ethylamino]-9a-methoxymitosane
(41) 7-[2-(4-Nitrophenyldithio)ethylamino]-9-a-methyloxy-1a-methylmitosane
(42) 7-[2-(4-Hydroxyphenyldithio)ethylamino]-9a-methoxymitosane
(43) 7-[2-Aminophenyldithio)ethylamino]-9a-methoxymitosane
(44) 7-[3-(3-Nitro-3-pyridyldithio)propylamino]-9a-methoxymitosane
(45) 7-[3-(4-Nitrophenyldithio)propylamino]-9a-methoxymitosane
(46) 4-[2-(4-Fluorophenyldithio)ethylamino]-9a-methoxymitosane
(47) 7-[2-(4-Bromophenyldithio)ethylamino]-9a-methoxymitosane
(48) 7-[2-(1-Phenylethyldithio)ethylamino]-9a-methoxymitosane
(49) 7-[2-(2-Carboxyethyldithio)ethylamino]-9a-methoxymitosane
(50) 7-[2-(2,4-Dichlorophenyldithio)ethylamino]-9a-methoxymitosane
(51) 7-[2-(3-Trifluoromethylphenyldithio)ethylamino]-9a-methoxymitosane
(52) 7-[2-(2,6-Dichlorophenyldithio)ethylamino]-9a-methoxymitosane
(53) 7-[2-(3-Aminophenyldithio)ethylamino]-9a-methoxymitosane
(54) 7-[2-(3-Methoxyphenyldithio)ethylamino]-9a-methoxymitosane

(55) 7-[2-(2-Chlorophenyldithio)ethylamino]-9a-methoxymitosane
(56) 7-[2-(2-Methoxyphenyldithio)ethylamino]-9a-methoxymitosane
(57) 7-[2-(2,5-Dichlorophenyldithio)ethylamino]9a-methoxymitosane
(58) 7-[2-(3-Chlorophenyldithio)ethylamino]-9a-methoxymitosane
(59) 7-[2-(3-Methyl-2-imidazolylmethyldithio)ethylamino]-9a-methoxymitosane
(60) 7-[2-(4-Pyridyldithio)ethylamino]-9a-methoxymitosane
(61) 7-[2-(3,4-Dichlorophenyldithio)ethylamino]-9a-methoxymitosane
(62) 7-[2-(2-Aminophenyldithio)ethylamino]-9a-methoxymitosane
(63) 7-[2-(4-Methyl-2-pyridylmethyldithio)ethylamino]-9a-methoxymitosane
(64) 7-[2-(4-Pyridylmethyldithio)ethylamino]-9a-methoxymitosane
(65) 7-[2-(2-Bromophenyldithio)ethylamino]-9a-methoxymitosane.

2. The compound of claim 1 identified as Compound No. 32.

3. The compound of claim 1 identified as Compound No. 33.

4. The compound of claim 1 identified as Compound No. 34.

5. The compound of claim 1 identified as Compound No. 35.

6. The compound of claim 1 identified as Compound No. 36.

7. The compound of claim 1 identified as Compound No. 37.

8. The compound of claim 1 identified as Compound No. 38.

9. The compound of claim 1 identified as Compound No. 39.

10. The compound of claim 1 identified as Compound No. 40.

11. The compound of claim 1 identified as Compound No. 41.

12. The compound of claim 1 identified as Compound No. 42.

13. The compound of claim 1 identified as Compound No. 43.

14. The compound of claim 1 identified as Compound No. 44.

15. The compound of claim 1 identified as Compound No. 45.

16. The compound of claim 1 identified as Compound No. 46.

17. The compound of claim 1 identified as Compound No. 47.

18. The compound of claim 1 identified as Compound No. 48.

19. The compound of claim 1 identified as Compound No. 49.

20. The compound of claim 1 identified as Compound No. 50.

21. The compound of claim 1 identified as Compound No. 51.

22. The compound of claim 1 identified as Compound No. 52.

23. The compound of claim 1 identified as Compound No. 53.

24. The compound of claim 1 identified as Compound No. 54.

25. The compound of claim 1 identified as Compound No. 55.

26. The compound of claim 1 identified as Compound No. 56.

27. The compound of claim 1 identified as Compound No. 57.

28. The compound of claim 1 identified as Compound No. 58.

29. The compound of claim 1 identified as Compound No. 59.

30. The compound of claim 1 identified as Compound No. 60.

31. The compound of claim 1 identified as Compound No. 61.

32. The compound of claim 1 identified as Compound No. 62.

33. The compound of claim 1 identified as Compound No. 63.

34. The compound of claim 1 identified as Compound No. 64.

35. The compound of claim 1 identified as Compound No. 65.

36. The pharmaceutically acceptable metal or amine salts of a compound of claim 1 selected from Compound Nos. 34, 35, 36, 37, and 38.

37. The sodium salt of a compound of claim 1 selected from Compound Nos. 34, 35, 36, 37, and 38.

38. The pharmaceutically acceptable acid addition salts of a Compound of claim 1 selected from Compound Nos. 33, 36, 37, 38, 40, 43, 53, 60, 62, 63, and 64.

* * * * *